(12) United States Patent
Rousseau et al.

(10) Patent No.: US 12,011,027 B2
(45) Date of Patent: Jun. 18, 2024

(54) RECONSTITUTED COCOA MATERIAL FOR GENERATING AEROSOL

(71) Applicant: Mativ Holdings, Inc., Alpharetta, GA (US)

(72) Inventors: Cedric Rousseau, Le Mans (FR); Cedric Jardin, Le Mans (FR); Doriane Bigot, Le Mans (FR)

(73) Assignee: SWM Holdings US, LLC, Alpharetta, GA (US)

( * ) Notice: Subject to any disclaimer, the term of this patent is extended or adjusted under 35 U.S.C. 154(b) by 325 days.

(21) Appl. No.: 16/788,095

(22) Filed: Feb. 11, 2020

(65) Prior Publication Data

US 2020/0253266 A1     Aug. 13, 2020

Related U.S. Application Data

(60) Provisional application No. 62/857,627, filed on Jun. 5, 2019, provisional application No. 62/803,908, filed on Feb. 11, 2019.

(51) Int. Cl.
| | |
|---|---|
| *A24D 1/18* | (2006.01) |
| *A24B 15/167* | (2020.01) |
| *A24D 1/20* | (2020.01) |
| *A61K 31/05* | (2006.01) |
| *A61K 31/352* | (2006.01) |

(52) U.S. Cl.
CPC ............. *A24B 15/167* (2016.11); *A24D 1/18* (2013.01); *A24D 1/20* (2020.01); *A61K 31/05* (2013.01); *A61K 31/352* (2013.01)

(58) Field of Classification Search
CPC ................................. A24B 15/16; A24D 1/18
See application file for complete search history.

(56) References Cited

U.S. PATENT DOCUMENTS

| | | |
|---|---|---|
| 2,418,296 A | 4/1947 | Frederickson |
| 3,012,914 A | 12/1961 | Battista et al. |
| 3,100,492 A | 8/1963 | Schmidt |
| 3,203,432 A | 8/1965 | Green et al. |

(Continued)

FOREIGN PATENT DOCUMENTS

| | | |
|---|---|---|
| CN | 1179922 | 4/1998 |
| CN | 103161091 | 6/2013 |

(Continued)

OTHER PUBLICATIONS

Co pending U.S. Appl. No. 16/998,514, filed Aug. 20, 2020.

(Continued)

*Primary Examiner* — Eric Yaary
(74) *Attorney, Agent, or Firm* — Dority & Manning, P.A.

(57) ABSTRACT

An aerosol generating material is disclosed containing a reconstituted cocoa bean husk material. The reconstituted material can contain extracted cocoa husk fibers in combination with web building fibers, such as softwood fibers. The reconstituted cocoa husk material is capable of generating an aerosol, such as a smoke, that has a very mild and neutral taste without any harsh components. The reconstituted cocoa husk material contains no nicotine and produces lower tar than conventional tobacco materials. The material can be used as a carrier for delivering various active agents in an aerosol generated by the material in a controlled, consistent and uniform manner.

21 Claims, 15 Drawing Sheets

(56) References Cited

U.S. PATENT DOCUMENTS

| | | | |
|---|---|---|---|
| 3,429,316 A | 2/1969 | Hess et al. | |
| 4,201,228 A | 5/1980 | Lewinger | |
| 4,279,824 A | 7/1981 | McKinney | |
| 4,459,998 A | 7/1984 | Labbe | |
| 4,542,755 A * | 9/1985 | Selke | A24B 3/14 131/365 |
| 4,564,031 A * | 1/1986 | Egri | A24B 15/42 131/358 |
| 4,681,126 A | 7/1987 | Strubel et al. | |
| 4,719,929 A | 1/1988 | Breckwoldt | |
| 4,813,438 A | 3/1989 | Fleming | |
| 4,969,477 A | 11/1990 | Yagisawa | |
| 4,987,906 A | 1/1991 | Young et al. | |
| 5,119,836 A | 6/1992 | White | |
| 5,135,010 A | 8/1992 | Fan | |
| 5,143,097 A | 9/1992 | Sohn et al. | |
| 5,159,942 A | 11/1992 | Brinkley et al. | |
| 5,203,355 A | 4/1993 | Clearman et al. | |
| 5,322,076 A | 6/1994 | Brinkley et al. | |
| 5,323,791 A | 6/1994 | Wu et al. | |
| 5,325,877 A | 7/1994 | Young et al. | |
| 5,327,917 A * | 7/1994 | Lekwauwa | A24B 15/165 131/297 |
| 5,339,838 A | 8/1994 | Young et al. | |
| 5,377,698 A | 1/1995 | Litzinger et al. | |
| 5,501,237 A | 3/1996 | Young et al. | |
| 5,513,663 A | 5/1996 | Van Leuven et al. | |
| 5,533,530 A | 7/1996 | Young et al. | |
| 5,562,108 A | 10/1996 | Hardy et al. | |
| 5,715,844 A | 2/1998 | Young et al. | |
| 5,908,034 A | 6/1999 | Adedeji | |
| 6,289,897 B1 | 9/2001 | McAdam et al. | |
| 6,679,270 B2 | 1/2004 | Baskevitch et al. | |
| 6,699,288 B2 | 3/2004 | Moret | |
| 7,323,197 B1 | 1/2008 | Lukacs | |
| 7,428,905 B2 | 9/2008 | Mua | |
| 7,836,896 B2 | 11/2010 | Nadimi | |
| 8,007,637 B2 | 8/2011 | Liu et al. | |
| 8,047,209 B2 | 11/2011 | May | |
| 8,469,038 B2 | 6/2013 | Sinclair, Jr. | |
| 8,646,461 B2 | 2/2014 | Von Bostel et al. | |
| 8,813,760 B2 | 8/2014 | May, Jr. | |
| 8,897,628 B2 | 11/2014 | Conley et al. | |
| 9,022,041 B2 | 5/2015 | Marsi | |
| 9,095,173 B2 | 8/2015 | Sinclair, Jr. | |
| 9,220,298 B1 | 12/2015 | En'Wezoh et al. | |
| 9,428,757 B2 | 8/2016 | Senger et al. | |
| 9,433,240 B2 | 9/2016 | Sinclair, Jr. | |
| 9,462,829 B2 | 10/2016 | Van Den Berg | |
| 9,474,725 B1 | 10/2016 | Reillo et al. | |
| 9,532,593 B2 | 1/2017 | Turner | |
| 9,655,381 B2 | 5/2017 | Sinclair, Jr. | |
| 9,675,103 B2 | 6/2017 | Sinclair, Jr. | |
| 9,839,612 B2 | 12/2017 | Reillo et al. | |
| 9,956,911 B2 | 5/2018 | Wright | |
| 9,972,680 B2 | 5/2018 | Reillo et al. | |
| 9,974,739 B2 | 5/2018 | Reillo et al. | |
| 10,016,360 B1 | 7/2018 | Elbogen et al. | |
| 10,076,135 B2 | 9/2018 | Lisauskas et al. | |
| 10,080,385 B2 | 9/2018 | Sinclair | |
| 10,165,795 B2 | 1/2019 | O'Malley | |
| 10,172,897 B2 | 1/2019 | Vu et al. | |
| 10,178,872 B2 | 1/2019 | Mompon | |
| 10,206,427 B2 | 2/2019 | Pijnenberg et al. | |
| 10,226,066 B2 | 3/2019 | Moldoveanu et al. | |
| 10,271,578 B2 | 4/2019 | John et al. | |
| 10,639,439 B2 | 5/2020 | Larson | |
| 10,729,662 B2 | 8/2020 | Ragot et al. | |
| 10,750,773 B2 | 8/2020 | Yang et al. | |
| 2004/0103908 A1 | 6/2004 | Prakash et al. | |
| 2004/0173229 A1 | 9/2004 | Crooks et al. | |
| 2004/0255965 A1 | 12/2004 | Perfetti et al. | |
| 2005/0034739 A1 * | 2/2005 | Dittrich | A24B 15/14 131/364 |
| 2005/0263165 A1 | 12/2005 | Oh et al. | |
| 2006/0021626 A1 | 3/2006 | Mua | |
| 2006/0185684 A1 * | 8/2006 | Albino | A24B 15/20 131/270 |
| 2008/0000488 A1 | 1/2008 | Nadimi et al. | |
| 2009/0050165 A1 | 2/2009 | Murali | |
| 2010/0187143 A1 * | 7/2010 | Essen | A24B 13/00 131/369 |
| 2012/0095088 A1 | 4/2012 | Hospodor | |
| 2012/0152264 A1 | 6/2012 | Coleman et al. | |
| 2012/0318286 A1 | 12/2012 | Lisauskas et al. | |
| 2013/0306087 A1 | 11/2013 | Rose et al. | |
| 2014/0103099 A1 * | 4/2014 | Snow | A24D 1/025 229/87.14 |
| 2014/0166028 A1 | 6/2014 | Fuisz et al. | |
| 2014/0216481 A1 | 8/2014 | Freeman | |
| 2014/0295049 A1 | 10/2014 | Ragot et al. | |
| 2014/0338680 A1 * | 11/2014 | Abramov | A24F 40/57 131/328 |
| 2014/0360520 A1 | 12/2014 | May | |
| 2015/0037389 A1 | 2/2015 | Ragot et al. | |
| 2015/0068544 A1 | 3/2015 | Moldoveanu et al. | |
| 2015/0083142 A1 | 3/2015 | Sinclair, Jr. | |
| 2015/0098906 A1 * | 4/2015 | Farrow | A24D 1/02 424/10.2 |
| 2015/0107614 A1 | 4/2015 | Sinclair, Jr. | |
| 2015/0114412 A1 * | 4/2015 | Dittrich | A24D 3/12 131/334 |
| 2015/0374030 A1 | 12/2015 | Lisauskas et al. | |
| 2016/0029690 A1 | 2/2016 | Sinclair | |
| 2016/0037823 A1 | 2/2016 | Ruben | |
| 2016/0193266 A1 | 7/2016 | Ablett | |
| 2016/0205993 A1 * | 7/2016 | Börjesson | A24B 13/00 |
| 2016/0255854 A1 | 9/2016 | Rousseau | |
| 2016/0302474 A1 | 10/2016 | Chen et al. | |
| 2016/0366926 A1 * | 12/2016 | Uren | A24B 3/12 |
| 2017/0035095 A1 * | 2/2017 | Zuchuat | A24B 15/12 |
| 2017/0112187 A1 | 4/2017 | Ostrander | |
| 2017/0112188 A1 | 4/2017 | Ostrander | |
| 2017/0112189 A1 | 4/2017 | Stern | |
| 2017/0119039 A1 | 5/2017 | Dena et al. | |
| 2017/0172201 A1 | 6/2017 | Turner | |
| 2017/0174404 A1 * | 6/2017 | Ragot | B65D 65/466 |
| 2017/0181466 A1 | 6/2017 | Batista | |
| 2017/0188623 A1 | 7/2017 | Cranford | |
| 2017/0202895 A1 | 7/2017 | Hugh | |
| 2017/0202896 A1 | 7/2017 | Hugh | |
| 2017/0245542 A1 | 8/2017 | Zappoli | |
| 2017/0258128 A1 | 9/2017 | Lisauskas et al. | |
| 2017/0273347 A1 | 9/2017 | Klipfel et al. | |
| 2017/0273349 A1 | 9/2017 | Moore | |
| 2017/0303576 A1 | 10/2017 | Rousseau | |
| 2017/0333503 A1 | 11/2017 | Ayres | |
| 2017/0347699 A1 | 12/2017 | Sinclair, Jr. | |
| 2018/0027869 A1 | 2/2018 | Scott | |
| 2018/0116276 A1 | 5/2018 | Prog et al. | |
| 2018/0137792 A1 | 5/2018 | Gransaull | |
| 2018/0168224 A1 | 6/2018 | Naughton et al. | |
| 2018/0177231 A1 * | 6/2018 | Woodbine | H04L 67/12 |
| 2018/0213838 A1 | 8/2018 | Richmond et al. | |
| 2018/0233558 A1 | 8/2018 | Reillo et al. | |
| 2018/0257801 A1 * | 9/2018 | Persson | B29C 66/0042 |
| 2018/0271826 A1 | 9/2018 | Sievers et al. | |
| 2018/0279666 A1 | 10/2018 | Aoun et al. | |
| 2018/0325972 A1 | 11/2018 | Moore | |
| 2018/0344790 A1 | 12/2018 | Vu et al. | |
| 2018/0352848 A1 | 12/2018 | Vu et al. | |
| 2018/0360099 A1 | 12/2018 | Ibrahim | |
| 2018/0360103 A1 | 12/2018 | Kaplan et al. | |
| 2019/0022158 A1 * | 1/2019 | Greenbaum | A61K 31/047 |
| 2019/0145050 A1 | 5/2019 | Rousseau et al. | |
| 2019/0262304 A1 | 8/2019 | Townsend et al. | |
| 2019/0380377 A1 | 12/2019 | Rabes | |
| 2020/0054064 A1 * | 2/2020 | Ajithkumar | A24B 15/14 |
| 2020/0101013 A1 | 4/2020 | Ragot et al. | |
| 2020/0108018 A1 | 4/2020 | Shadurin et al. | |
| 2020/0138090 A1 * | 5/2020 | Deforel | A24B 15/165 |
| 2020/0178590 A1 * | 6/2020 | Wu | D21H 27/00 |
| 2020/0179269 A1 | 6/2020 | Tamir et al. | |
| 2020/0197639 A1 | 6/2020 | Larson | |

(56) References Cited

U.S. PATENT DOCUMENTS

| | | |
|---|---|---|
| 2020/0205463 A1 | 7/2020 | Lamblin |
| 2020/0236989 A1* | 7/2020 | Prince .................. A24D 1/18 |
| 2020/0253264 A1 | 8/2020 | Rousseau et al. |
| 2020/0253267 A1 | 8/2020 | Rousseau et al. |
| 2020/0253268 A1 | 8/2020 | Rousseau et al. |
| 2020/0253269 A1 | 8/2020 | Rousseau et al. |
| 2020/0253566 A1 | 8/2020 | Otomaru et al. |
| 2020/0275688 A1 | 9/2020 | Rousseau |
| 2020/0297023 A1 | 9/2020 | Billon et al. |

FOREIGN PATENT DOCUMENTS

| | | |
|---|---|---|
| CN | 103704882 | 4/2014 |
| CN | 103141928 B | 8/2015 |
| EP | 0336458 | 10/1989 |
| EP | 0337506 | 10/1989 |
| EP | 0339689 | 11/1989 |
| EP | 02710036 | 3/1992 |
| EP | 1797779 | 6/2006 |
| EP | 1420659 | 6/2007 |
| EP | 3586649 A1 | 1/2020 |
| GB | 884435 A | 12/1961 |
| GB | 195634 A | 6/1970 |
| IN | 3540DEL2012 | 12/2012 |
| JP | S52117499 A | 10/1977 |
| JP | 6356244 B2 | 9/2016 |
| WO | WO2002047494 | 6/2002 |
| WO | WO2003020057 | 3/2003 |
| WO | WO2004043173 | 5/2004 |
| WO | WO2004068974 | 8/2004 |
| WO | WO2006097447 | 9/2006 |
| WO | WO2011127679 | 10/2011 |
| WO | WO2011127680 | 10/2011 |
| WO | WO2014106819 | 7/2014 |
| WO | WO2016026810 | 2/2016 |
| WO | WO2016050873 | 4/2016 |
| WO | WO2016171997 | 10/2016 |
| WO | WO2018178978 | 10/2018 |
| WO | WO2018143952 | 8/2019 |
| WO | WO2020/097430 | 5/2020 |

OTHER PUBLICATIONS

AFT, "Pulp Freeness Conversion Chart," Accessed Aug. 22, 2022, Retrieved from: https://aft-global.com/en/resources/pulp-freeness-conversion-chart.

Japanese Office Action Corresponding to Application No. 2021-546665 on Mar. 5, 2024.

* cited by examiner

RECONSTITUTED COCOA MATERIAL FOR GENERATING AEROSOL

RELATED APPLICATIONS

The present application is based on and claims priority to U.S. Provisional Patent Application Ser. No. 62/857,627, filed on Jun. 5, 2019 and U.S. Provisional Patent Application Ser. No. 62/803,908, filed on Feb. 11, 2019, both of which are incorporated herein by reference.

BACKGROUND

Conventional smoking articles, such as cigarettes, cigars, and pipes, combust a tobacco material at temperatures that release volatile compounds, which are inhaled through the mainstream smoke. The mainstream smoke delivered to the user not only has a characteristic taste that smokers enjoy, but also can deliver to the user volatile compounds that are absorbed into the blood through the lungs. The volatile compounds can provide the smoker with a pleasant and calming effect. For example, tobacco materials can contain over 3,000 potential physiologically active compounds, including nicotine.

In addition to tobacco-based smoking articles, recently various non-tobacco smoking articles have been proposed. For instance, one alternative to producing smoking articles using tobacco materials is to replace the tobacco with an herbal composition. The herbal composition can be formulated so as to be nicotine-free. Such herbal smoking articles, for instance, can contain turmeric, clove, licorice, ginger, sandalwood, cinnamon, or cumin. Although herbal smoking articles can have lower nicotine levels, many of the smoking articles produce a harsh taste when combusted or heated. In addition, many herbal smoking articles are completely devoid of any active compounds which makes them unappealing to many smokers.

Recently, Canada and many states in the United States have legalized the use of *cannabis* for medical and/or recreational use. In the medical sphere, *cannabis* contains various cannabinoids that are more and more becoming legitimate pain relief alternatives to the use of conventional pain medications, such as opioids. *Cannabis* contains, for instance, tetrahydrocannabinol (THC) and cannabidiol (CBD). THC acts on specific receptors in the brain which can lead to a feeling of euphoria and a relaxed state. CBD also interacts with pain receptors in the brain. CBD, however, does not create the same euphoric feeling caused by THC. CBD, however, exerts pain-relieving and anti-inflammatory effects.

In view of recent legislation, those skilled in the art have attempted to produce improved aerosol-producing articles, such as smoking articles, made from *cannabis*. Various problems exist, however, in delivering *cannabis* components to a patient or a user through inhaling an aerosol. For example, THC and/or CBD deliveries can vary dramatically depending upon the particular plant and the particular plant parts used to produce the aerosol or smoke. Simply rolling a *cannabis* material in a rolling paper, for instance, can lead to drastic non-uniformity differences in delivery based upon many factors including the paper used, packing densities, the parts of the plants used, the manner in which the plants have been prepared, and the like. Further, in addition to THC and CBD, *cannabis* contains over 60 different cannabinoid compounds and over 400 other different compounds that may give the product a bad taste and/or a harsh smoking experience.

In view of the above, a need currently exists for an improved aerosol generating material that can control the delivery of physiologically active compounds in an aerosol generated by the product. In particular, a need exists for an aerosol generating material that can control the delivery of various active compounds, such as nicotine, THC, CBD, flavorants, and the like through an aerosol. More particularly, a need exists for an aerosol generating material capable of delivering active compounds not only in a uniform and consistent manner, but also at desired levels while also providing a pleasant or neutral taste.

SUMMARY

In general, the present disclosure is directed to an aerosol generating material that can control and regulate the amount of active compounds delivered to a user when the material is incorporated into an aerosol-producing article. The aerosol-producing article, for instance, may be a smoking article or a "heat but not burn" article.

In one embodiment, the aerosol generating material includes a reconstituted cocoa husk material containing extracted cocoa husk fibers combined with web building fibers. The web building fibers may comprise delignified cellulosic fibers, such as softwood fibers, hardwood fibers, or mixtures thereof.

In accordance with the present disclosure, the aerosol generating material further includes an aerosol delivery composition applied to the reconstituted cocoa husk material. The aerosol delivery composition contains an aerosol delivery agent. When the aerosol generating material produces an aerosol, the aerosol delivery agent is contained in the aerosol in controlled amounts.

The aerosol delivery agent can be in the form of an oil or a solid and may comprise a drug or a flavorant. Aerosol delivery agents that can be applied to the reconstituted cocoa husk material include nicotine, a cannabinoid, such as tetrahydrocannabinol, cannabidiol, or mixtures thereof, a sugar, a licorice extract, honey, a coffee extract, maple syrup, a tea extract, a plant extract, a botanical extract, a tobacco extract, a fruit extract, or combinations thereof. The aerosol delivery agent can be present on the reconstituted cocoa husk material in an amount greater than about 0.1% by weight, such as in an amount greater than about 1% by weight, such as in an amount greater than about 3% by weight, such as in an amount greater than about 5% by weight, such as in an amount greater than about 10% by weight, such as in an amount greater than about 15% by weight, such as in an amount greater than about 20% by weight, such as in an amount greater than about 25% by weight, such as in an amount greater than about 30% by weight, such as in an amount greater than about 35% by weight, such as in an amount greater than about 40% by weight, and generally in an amount less than about 50% by weight.

The reconstituted cocoa husk material contains extracted cocoa husk fibers combined with web building fibers. The web building fibers can comprise delignified cellulosic fibers, such as softwood fibers, hardwood fibers, or mixtures thereof. The reconstituted cocoa husk material contains water soluble cocoa husk components in an amount of less than about 50% by weight, such as in an amount of less than 10% by weight. In addition, the aerosol generating material can contain a humectant. The humectant, for instance, may comprise glycerol, propylene glycol, or mixtures thereof. The humectant can be present in various amounts. For instance, in one embodiment, the humectant can be present in an amount of about 5% by weight or less. Alternatively, the humectant may be present in an amount of greater than about 5% by weight, such as greater than about 10% by weight, such as greater than about 20% by weight, and generally in an amount less than about 50% by weight.

The web building fibers, in addition to being wood pulp fibers, may comprise flax fibers, hemp fibers, abaca fibers, bamboo fibers, coconut fibers, ramie fibers, jute fibers, or mixtures thereof. The web building fibers can be present in the reconstituted cocoa husk material in an amount greater than about 20% by weight, such as in an amount greater than about 30% by weight, such as in an amount greater than about 40% by weight, and generally in an amount less than about 70% by weight. The web building fibers, for example, can be present in the reconstituted cocoa husk material in an amount less than about 35% by weight, such as in an amount less than about 30% by weight, such as in an amount less than about 28% by weight, and generally in an amount greater than about 20% by weight, such as in an amount greater than about 23% by weight.

The amount of web building fibers present in the reconstituted cocoa husk material can depend upon the amount of water soluble components. For instance, in one embodiment, when the reconstituted cocoa husk material contains water soluble components in an amount less than about 10% by weight, the web building fibers can be present in the material in an amount from about 25% to about 30% by weight, while cocoa husk fibers can be present in the material in an amount from about 65% to about 70% by weight. When the reconstituted cocoa husk material contains greater than 10% by weight water soluble components, on the other hand, the material can contain web building fibers in an amount from about 20% to about 25% by weight and can contain cocoa husk fibers in an amount from about 53% to about 57% by weight. The above embodiments, however, are merely exemplary and the relative amounts of each of the fibers can vary.

The reconstituted cocoa husk material can have a basis weight of generally from about 40 gsm to about 120 gsm, such as from about 55 gsm to about 85 gsm. The basis weight, for instance, can be less than about 83 gsm, such as less than about 80 gsm, such as less than about 78 gsm, such as less than about 70 gsm, and generally greater than about 55 gsm, such as greater than about 58 gsm. In one embodiment, the reconstituted cocoa husk material can be treated with a burn control agent. The reconstituted cocoa husk material can be in the form of a filler material such as in the form of a strip, strips, shreds, or mixtures thereof.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

DEFINITIONS

Figure 1:
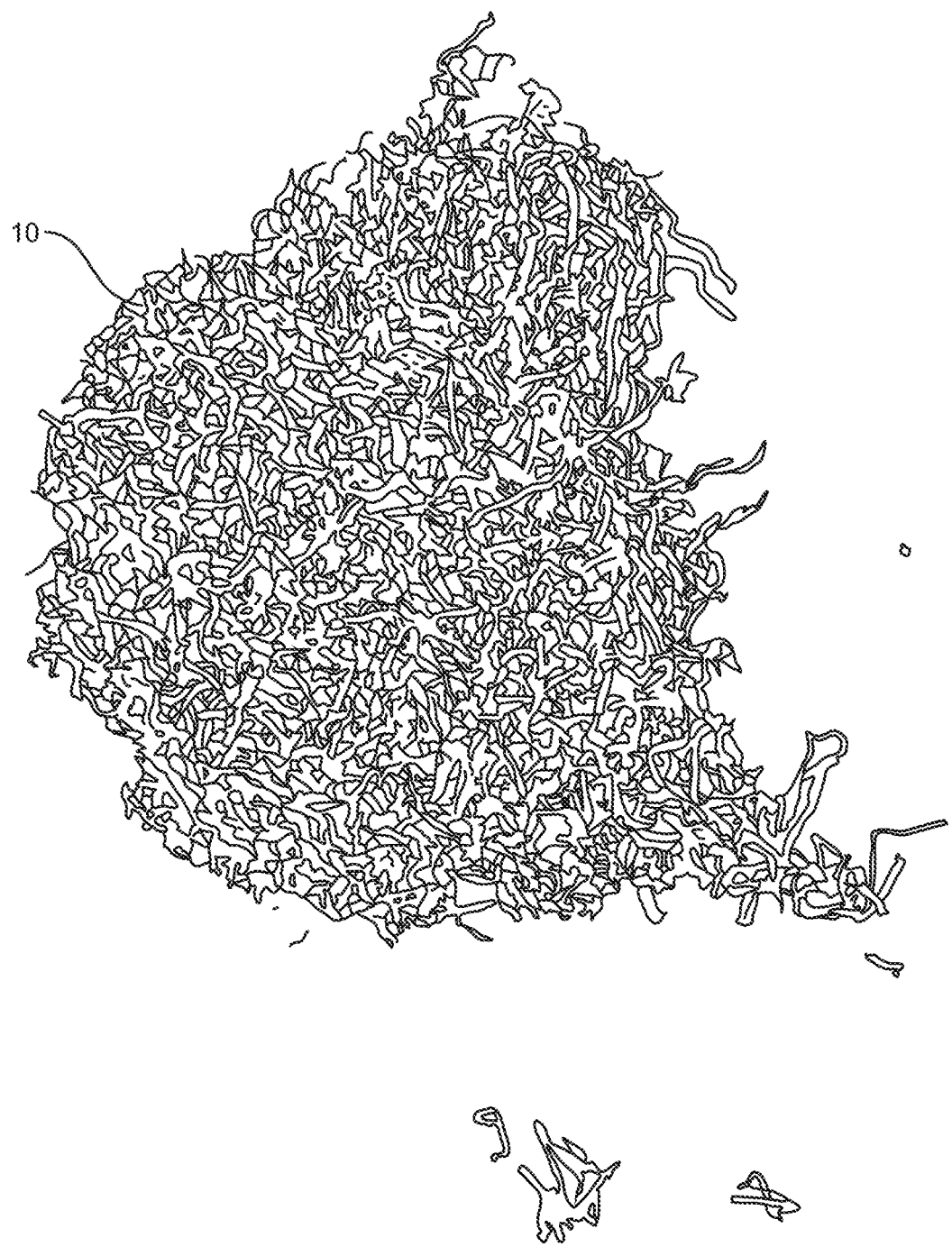
FIG. 1 is a perspective view of one embodiment of a reconstituted plant material made in accordance with the present disclosure.

As used herein, a "reconstituted plant material" refers to a material formed by a process in which a plant feed stock, such as cocoa shells, is extracted with a solvent to form an extract of solubles, such as water solubles, and an extracted insoluble portion or residue comprising fibrous material. The extracted and insoluble fibrous material is then formed into a sheet through any suitable process and the extract may either be discarded or reapplied to the formed sheet. The extract can be fed through various processes for concentrating the extract and optionally removing or adding various components prior to being recombined with the fibrous material. In the present disclosure, the reconstituted plant material is formed from extracted cocoa husk fibers combined with web building fibers, such as cellulose fibers. The extract of solubles obtained from the cocoa husk fibers is optionally reapplied to the sheet.

As used herein, an "aerosol generating material" is meant to include both a combustible material that undergoes combustion in a smoking article and to an aerosol-forming material that is heated but not combusted to form an inhalable aerosol. Combustible smoking articles can include cigarettes, cigarillos and cigars. In a cigarette, the aerosol generating material is surrounded by a wrapping material to form a smokable rod. Aerosol generating devices for generating an aerosol include, for instance, devices in which an aerosol is generated by electrical heating or by the transfer of heat from a combustible fuel element or heat source to heat but not burn the aerosol generating material, which releases volatile compounds. As the released compounds cool, they condense to form an aerosol that is inhaled by the consumer.

As used herein, "extracted cocoa husk fibers" refers to cocoa husk fibers that have been subjected to an extraction process in which the cocoa husk has been contacted with an aqueous solution to remove water soluble components contained in the cocoa husks. The extraction process is different from a delignification process and from a bleaching treatment.

As used herein, "delignified" cellulosic fibers refers to fibers that have been subjected to a pulping or delignification process by which the cellulose fibers are separated from the plant material through chemical means, mechanical means, or through a combination of chemical and mechanical means.

As used herein, the term "refine" is used to mean that the plant material is subjected to a mechanical treatment that modifies the fibers of the material so that they are better suited to forming a fibrous sheet or substrate. Refining can be accomplished using a conical refiner, disks refiner or a beater, such as a Valley beater. The mechanical process exerts an abrasive and bruising action on the plant material such that the plant material is deformed and declustered. Refining is a different process than delignification and pulping.

As used herein, the term "stalk" is used to refer to the main structural portion of a plant that remains after the leaves have been removed.

As used herein, the term "stem" is used herein to refer to the structural portion of a plant connecting the leaves or laminae to the stalk and also to the veins or ribs that extend through the leaves. The term "stem" does not encompass the term "stalk" and vice versus.

As used herein, "*cannabis*" may refer to any variety of the *Cannabis* plant, such as *Cannabis sativa* or *Cannabis indica*, for instance. More particularly, the present disclosure may refer to leaves, stems, seeds and flowers or any other part of the *Cannabis* plant, as *cannabis*. Nonetheless, *cannabis*, as referred to herein, includes *cannabis* that contains average or high levels of THC and/or CBD (usually known as marijuana), hemp, which may contain low, or very low, levels of THC, industrial hemp, which may refer to a *cannabis* plant that contains less than 0.3% THC, or combinations thereof.

The Freeness value (° SR) measures generally the rate at which a dilute suspension of refined fibers may be drained. The freeness is measured by the Schopper Riegler Method for drainability. As used herein, freeness is measured according to Test NORM EN ISO 5267-1.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to an aerosol generating material that can regulate the amount of active compounds delivered to a user when the material is incorporated into an aerosol-producing article, such as a smoking article or a heat but not burn aerosol generating device. In one embodiment, the material comprises a reconstituted plant material made from extracted cocoa husk fibers combined with web building fibers. The extracted cocoa husks can be combined with the web building fibers to produce a reconstituted sheet that, in one embodiment, can be cut or shredded to form a loose filler material that is designed to generate an aerosol when heated or burned.

The reconstituted cocoa husk material of the present disclosure offers many advantages and benefits. For instance, the reconstituted material is nicotine free, meaning that the material produces an aerosol when heated or burned that contains undetectable levels of nicotine. In addition, the reconstituted cocoa husk material produces lower levels of tar than conventional tobacco fillers. In addition, the reconstituted plant material has a very neutral taste when smoked. Mainstream smoke or an aerosol generated by the reconstituted plant material, for instance, produces a pleasant smoking or aerosol experience with an enjoyable and neutral taste while being completely devoid of any harsh components. In one embodiment, the reconstituted material produces an aerosol with a roasted cocoa bean smell or taste.

Because the reconstituted plant material has a neutral taste when smoked, the reconstituted material is well suited to being combined with other smokable fillers and/or topical additives. For example, the reconstituted cocoa husk material can be combined with tobacco materials for forming an aerosol producing filler that has a tobacco taste that consumers desire while having controlled nicotine levels. For instance, the proportion of the reconstituted cocoa husk material of the present disclosure can be increased or decreased for controlling nicotine levels when combined with a tobacco material. When combined with a tobacco material, the reconstituted plant material of the present disclosure, due to its neutral characteristics, does not in any way mask the taste of the tobacco materials and, in fact, can enhance the smoking or aerosol experience by diluting and decreasing irritants in addition to reducing nicotine levels.

In addition to regulating nicotine levels, the reconstituted cocoa husk material of the present disclosure can similarly be used to regulate the levels of other active compounds and/or to improve the taste of other non-tobacco filler materials. For example, the reconstituted cocoa husk material can be combined with an herbal filler for improving one or more aspects of the herbal filler.

In addition, the reconstituted cocoa husk material is well suited as a carrier for receiving an active agent that is then delivered to a user through an aerosol during burning or heating of the material in a consistent and uniform manner. For example, the reconstituted cocoa husk material can be used to deliver and regulate various drugs and flavorants to a user. In one embodiment, for instance, the reconstituted cocoa husk material of the present disclosure can be used as a delivery vehicle for delivering controlled amounts of *cannabis* cannabinoids, such as THC and CBD, in a uniform and consistent manner.

As described above, the reconstituted plant material of the present disclosure is generally formed from extracted cocoa husks combined with web building fibers. Cocoa materials for use in the present disclosure are obtained from *Theobroma cacao*, which is also referred to as the cacao tree. The cacao tree is in the evergreen family and is native to tropical regions. The cacao tree produces a fruit, referred to as a cacao pod. Cacao pods are generally yellow to orange in color and can weigh over one pound when ripe. The pod contains anywhere from 10 to about 80 cocoa beans that are used to produce chocolate, juices, jelly, and the like. After the beans are removed from the cacao pod, the cocoa beans are dried and cured or fermented by being exposed to sunlight and/or ultraviolet light. Each individual bean is covered in a husk or shell. The husk or shell is removed from the bean prior to using the bean for producing food products. The reconstituted plant material of the present disclosure is made from the cocoa shells or husks, although other components of the cacao pod may also be used.

The cocoa shell or husk contains fibers which are well suited to producing substrates and web materials. In one embodiment, the cocoa husks are optionally sized or ground and then subjected to an extraction process for removing water soluble components. The extracted cocoa husks can then be combined with web building fibers and formed into a substrate, such as a reconstituted sheet. The substrate can optionally be treated with the extract obtained from the cocoa husks. Alternatively, the extract obtained from the cocoa husks can be discarded and not recombined with the water insoluble fibers and other materials. The reconstituted material is then dried and formed into an aerosol generating material, such as a smokable filler. The aerosol generating material can then optionally be combined with various other components. For instance, the material can be treated with various aerosol delivery agents and/or combined with various other aerosol or smoking fillers, such as tobacco materials or other herbal fillers.

The resulting aerosol generating material made in accordance with the present disclosure can then be used in numerous different types of consumer products. For instance, in one embodiment, the aerosol generating material can be incorporated into smoking articles, such as cigarettes, cigarillos, cigars, and the like. In one embodiment, the aerosol generating material of the present disclosure can be packaged and sold as a loose filler material for use in pipes or to allow consumers to roll their own cigarettes or other smoking articles. In an alternative embodiment, the aerosol generating material of the present disclosure can be incorporated into devices that heat the material without burning the material to produce an aerosol that is inhaled. The aerosol generating material can be cut, shredded, or otherwise processed into a form best suited for the particular application and product.

In forming the reconstituted plant material of the present disclosure, the cocoa shells or husks are first collected and optionally reduced in size. For example, in one embodiment, the cocoa components can be subjected to a grinding operation, milling operation or beating operation that can reduce the size of the cocoa components and/or reduce the cocoa husks into individual fibers. For example, in one embodiment, the cocoa materials including the cocoa shells can be fed to a hammer mill that beats the cocoa materials against a screen for producing a fibrous material.

After the cocoa husk is optionally reduced in size, the cocoa husk is subjected to an extraction process for removing water soluble components. The extraction process can provide various different benefits. For instance, the extraction process can remove from the cocoa husk pectin which makes it easier to process the cocoa husk into a fiber substrate or a reconstituted plant sheet. It is believed that removing the pectin from the cocoa husk also contributes to the neutral taste of the final product.

Subjecting the cocoa husk to an extraction process also cleans the husk and removes any herbicides, pesticides and/or microorganisms that may be present on the material.

During the extraction process, the cocoa husk is contacted with a solvent in order to remove the water soluble components. In one embodiment, the solvent comprises only water. In an alternative embodiment, various solvents that are water-miscible, such as alcohols (e.g., ethanol), can be combined with water to form an aqueous solvent. The water content of the aqueous solvent can, in some instances, be greater than 50 wt. % of the solvent, and particularly greater than 90 wt. % of the solvent. Deionized water, distilled water or tap water may be employed.

In addition to aqueous solvents, various other non-aqueous solvents may also be used. For example, in other embodiments, oils and fats may be used as the solvent. The oils and fats can be used alone or in combination with water to form a two-phase solvent.

The amount of the solvent in the suspension can vary widely, but is generally added in an amount from about 50 wt. % to about 99 wt. %, in some embodiments from about 60 wt. % to about 95 wt. %, and in some embodiments, from about 75 wt. % to about 90 wt. % of the suspension. However, the amount of solvent can vary with the nature of the solvent, the temperature at which the extraction is to be carried out, and the type of cocoa furnish.

After forming the solvent/cocoa furnish mixture, some or all of a soluble fraction of the furnish mixture may be separated from the mixture. The aqueous solvent/cocoa furnish mixture can be agitated by stirring, shaking or otherwise mixing the mixture in order to increase the rate of solubilization. Typically, the process is carried out for about one-half hour to about 6 hours. Process temperatures may range from about 10° C. to about 100° C., such as from about 40° C. to about 90° C.

After the cocoa materials are soaked in an extractant, the insoluble cocoa material can be mechanically separated from the cocoa liquor or extract using a press. Once the soluble fraction is separated from the cocoa furnish or insoluble fraction, the soluble fraction can be discarded or further processed, such as by being concentrated. The soluble fraction can be concentrated using any known type of concentrator, such as a vacuum evaporator. In one embodiment of the present disclosure, the soluble fraction can be highly concentrated. In one embodiment, for instance, the cocoa soluble fraction can be evaporated so as to have a final brix of from about 10% to about 50%, such as from about 15% to about 35%.

The resulting concentrated cocoa soluble fraction may be used in a separate process, or can be later coated onto the reconstituted plant material of the present disclosure as will be described in greater detail below.

The resulting water insoluble cocoa fraction is generally in an unrefined state. The cocoa material can comprise particles and fibers. In one embodiment, the insoluble and extracted cocoa fraction can be subjected to a refining process. For instance, the extracted cocoa husk material can be fed through any suitable refining device, such as a conical refiner or disks refiner. Other refining devices that may be used include a beater, such as a Valley beater. Refining can occur while the cocoa materials are moist or after being combined with water. For instance, in one embodiment, refining can occur while the cocoa husk material is at a consistency of less than about 10%, such as less than about 5%, such as less than about 3%.

In accordance with the present disclosure, the extracted cocoa husk material is then combined with web building fibers in forming a fiber substrate, such as a reconstituted plant material. For example, the extracted cocoa husk can be combined with water or an aqueous solution to form a slurry or pulp suspension. The web building fibers, such as delignified cellulosic fibers, can be combined with the cocoa husk material in forming the slurry. The web building fibers can be combined with the extracted cocoa husk material and subjected to a refining process. Alternatively, the extracted cocoa husk material can be fed through a refining process and then combined with the web building fibers. In still another aspect, the extracted cocoa husk material can be fed through a refining process, combined with web building fibers, and then fed through a further refining process.

The amount the extracted cocoa husk material and/or the web building fibers are refined can impact various properties of the reconstituted material formed later. For instance, increasing the amount the cocoa husk material and/or the web building fibers are refined can make it easier to cut and shred the reconstituted material. In addition, increasing the amount of refining can also help trap particles and prevent particle loss during handling of the reconstituted material.

In one aspect, the cocoa husk material and the web building fibers together can have a refining level or refining degree of greater than about 60° SR, such as greater than about 65° SR, such as greater than about 70° SR, such as greater than about 75° SR. The refining level can generally be less than about 100° SR, such as less than about 90° SR, such as less than about 80° SR.

The fiber slurry containing the extracted cocoa husk fibers and the web building fibers is used to form a continuous reconstituted sheet. For example, in one embodiment, the fiber slurry is fed to a papermaking process that can include a forming wire, gravity drain, suction drain, a felt press, and a dryer, such as a Yankee dryer, a drum dryer, or the like. For example, in one embodiment, the fiber slurry is formed into a continuous sheet on a Fourdrinier table. One advantage to combining the extracted cocoa husk with the cellulosic fibers is that the resulting fiber furnish can be processed on conventional papermaking equipment.

In one embodiment, the fiber slurry is laid onto a porous forming surface and formed into a sheet. Excess water is removed by a gravity drain and/or a suction drain. In addition, various presses can be used to facilitate water removal. The formed sheet can be dried and further treated.

Reconstituted substrates can also be made using various other different methods. For example, in one embodiment, the extracted cocoa husks and web building fibers may be extruded into a reconstituted material. In one embodiment, the reconstituted material can also be subjected to an expansion process. Expanded sheets can be made using, for instance, a gas, such as carbon dioxide, or by using a foaming agent. Suitable expansion mediums include starch, pullulan or other polysaccharides, solid foaming agents, inorganic salts and organic acids that provide in situ gaseous components, organic gaseous agents, inorganic gaseous agents, and volatile liquid foaming agents. Extruding also allows for the formation of rods or strands in addition to sheet materials.

In one aspect, the reconstituted plant material can be formed according to a cast leaf process. In a cast leaf process, the plant material is shredded and then blended with other materials, such as a binder, and formed into a slurry. Web building fibers can be contained within the slurry. To form a web of material, the slurry is transferred to a sheet forming apparatus. The sheet forming apparatus can be a continuous belt where the slurry may be continuously spread onto the belt. The slurry is distributed on the surface to form a sheet. The sheet is then dried, such as by using heat. The sheet can be wound onto a bobbin, trimmed, slitted or otherwise manipulated for forming products.

Optionally, the reconstituted plant material that is produced can also be treated with the cocoa soluble portion, such as a concentrated cocoa soluble portion that was separated from the insoluble fraction. The cocoa soluble portion can be applied to the web using various application methods, such as spraying, using a size press, saturating, etc. The amount of water soluble cocoa extracts applied to the reconstituted material can depend upon various factors and the anticipated end use application. In general, the water soluble cocoa extracts can be applied to the reconstituted plant material in an amount insufficient to adversely interfere with the neutral taste of the underlying material.

In one embodiment, the water soluble cocoa extracts are applied to the reconstituted material such that the reconstituted material contains water soluble cocoa extracts in an amount up to about 10% by weight, such as in an amount less than about 8% by weight, such as in an amount less than about 6% by weight, such as in an amount less than about 4% by weight, such as in an amount less than about 2% by weight, such as in an amount less than about 1% by weight and generally in an amount greater than about 0.5% by weight.

In one embodiment, greater amounts of water soluble cocoa extracts may be applied to the reconstituted material. For instance, in an alternative embodiment, the water soluble cocoa extracts are applied to the reconstituted material such that the reconstituted material contains the water soluble cocoa extracts in an amount greater than about 8% by weight, such as in an amount greater than about 10% by weight, such as in an amount greater than about 12% by weight, and generally in an amount less than about 25% by weight, such as in an amount less than about 23% by weight, such as in an amount less than about 21% by weight, such as in an amount less than about 20% by weight, such as in an amount less than about 18% by weight.

As described above, the reconstituted plant material of the present disclosure generally contains extracted cocoa husk fibers in combination with web building fibers. The web building fibers are incorporated into the reconstituted plant material or fiber substrate in an amount sufficient to provide strength and integrity to the resulting material. Web building fibers can also be incorporated into the reconstituted plant material so as to trap and prevent cocoa fibers and other cocoa components from separating from the fiber substrate. In general, the web building fibers can be any fibers suitable for improving at least one physical property of the reconstituted material.

Various different types of web building fibers may be used. In one embodiment, the web building fibers are delignified cellulosic fibers. For instance, the web building fibers may comprise wood pulp fibers such as softwood fibers or hardwood fibers. Other cellulosic fibers that may be used include flax fibers, hemp fibers, abaca fibers, bamboo fibers, coconut fibers, cotton fibers, kapok fibers, ramie fibers, jute fibers, or mixtures thereof. In one particular embodiment, the reconstituted plant material contains softwood fibers alone or in combination with other fibers such as hardwood fibers, abaca fibers, or the like.

In general, the web building fibers are present in the reconstituted plant material in an amount greater than about 10% by weight, such as in an amount greater than about 15% by weight, such as in an amount greater than about 20% by weight, such as in an amount greater than about 25% by weight, such as in an amount greater than about 30% by weight, such as in an amount greater than about 35% by weight, such as in an amount greater than about 40% by weight. The web building fibers are generally present in the reconstituted plant material in an amount less than about 70% by weight, such as in an amount less than about 60% by weight, such as in an amount less than about 55% by weight, such as in an amount less than about 50% by weight.

In one aspect, the amount of web building fibers selected for use in the reconstituted plant material can be in an amount sufficient to provide integrity to the reconstituted material. Greater amounts of web building fibers, however, can increase the difficulty in cutting or shredding the material. Increased amounts of web building fibers can also lead to the production of an aerosol that has a "paper" taste. In view of the above considerations, in one aspect, the web building fibers are present in the reconstituted plant material in an amount generally greater than about 18% by weight, such as in an amount greater than about 20% by weight, such as in an amount greater than about 22% by weight. The web building fibers, however, can also be present in an amount less than about 30% by weight, such as in an amount less than about 28% by weight, such as in an amount less than about 26% by weight. For example, the web building fibers can be present in the reconstituted plant material in one aspect in an amount from about 20% to about 25% by weight. In another aspect, the web building fibers can be present in the reconstituted plant material in an amount from about 23% to about 27% by weight.

In one embodiment, the web building fibers incorporated into the reconstituted plant material include a combination of longer fibers and shorter fibers. The longer fibers can generally have an average length of greater than about 2 mm, while the shorter fibers can generally have an average length of less than about 1.5 mm. The longer fibers can be used to improve strength and integrity, while the shorter fibers can better retain the cocoa fibers and other components within the fiber substrate. In one embodiment, for instance, the short fibers may be present in the reconstituted plant material in an amount greater than about 5% by weight, such as in an amount greater than about 10% by weight, and generally in an amount less than about 20% by weight. The longer fibers, on the other hand, can be present in the reconstituted web material in an amount greater than about 5% by weight, such as greater than about 10% by weight, such as in an amount greater than about 20% by weight, and generally in an amount less than about 50% by weight, such as in an amount less than about 40% by weight. In one embodiment, the shorter fibers comprise hardwood fibers, while the longer fibers comprise softwood fibers. The weight ratio between the longer fibers and the shorter fibers, for example, can be from about 6:1 to about 1:2, such as from about 6:1 to about 1:0.75. For instance, the weight ratio between the longer fibers (e.g. softwood fibers) and the shorter fibers (e.g. hardwood fibers) can be from about 4:1 to about 1:1. As described above, the total amount of web building fibers contained in the reconstituted plant material can be, in one aspect, from about 18% to about 30%, such as from about 20% to about 28% by weight in conjunction with the above weight ratios.

In one embodiment, the reconstituted web material can further contain a humectant. The humectant can be incorporated into the reconstituted plant material for various different reasons in order to provide different benefits and advantages. For instance, in one embodiment, a humectant may be incorporated into the reconstituted plant material in order to improve the processability and handling of the resulting fiber substrate. In an alternative embodiment, a humectant can be added to the reconstituted plant material in greater amounts so that the material is well suited for use in applications where the material is heated but not burned in order to produce an inhalable aerosol.

Various different humectants can be incorporated into the reconstituted plant material. The humectant, for instance, may comprise glycerol, propylene glycol, or mixtures thereof. Other humectants that may be used include sorbitol, triethylene glycol, lactic acid, glyceryl diacetate, glyceryl triacetate, triethyl citrate, isopropyl myristate, and mixtures thereof including mixtures with glycerol and/or propylene glycol.

As described above, the amount of humectant applied to the reconstituted plant material can depend upon various factors. In one embodiment, for instance, the humectant is present on the reconstituted plant material in an amount less than about 5% by weight, such as in an amount less than about 3% by weight, and generally in an amount greater than about 1% by weight. In other embodiments, the humectant may be present on the plant material in an amount greater than about 5% by weight, such as in an amount greater than about 10% by weight, such as in an amount greater than about 15% by weight, such as in an amount greater than about 20% by weight, and generally in an amount less than about 50% by weight, such as in an amount less than about 40% by weight, such as in an amount less than about 30% by weight, such as in an amount less than about 25% by weight. When added to the reconstituted plant material in an amount from about 10 to 40% by weight, such as in an amount from about 12 to about 30% by weight, such as in an amount from about 15 to about 25% by weight, the humectant serves as an aerosol generating agent that facilitates formation of an aerosol when the reconstituted plant material is heated without being combusted. In still another aspect, the humectant can be present in the reconstituted plant material in an amount from about 3% to about 8% by weight, such as in an amount from about 4% to about 6% by weight.

The reconstituted plant material of the present disclosure can also contain various other optional components. For example, in one embodiment, the reconstituted plant material can optionally be treated with a burn control agent. The burn control agent can control the burn rate of the material and/or can serve as an ash conditioner for improving the coherency and/or color of the ash that is produced when the material is combusted.

The burn control agent, for instance, may comprise a salt of a carboxylic acid. For example, the burn control agent may comprise an alkali metal salt of a carboxylic acid, an alkaline earth metal salt of a carboxylic acid, or mixtures thereof. Examples of burn control agents that may be used include a salt of acetic acid, citric acid, malic acid, lactic acid, tartaric acid, carbonic acid, formic acid, propionic acid, glycolic acid, fumaric acid, oxalic acid, malonic acid, succinic acid, nitric acid, phosphoric acid, or mixtures thereof. Particular burn controlling agents that may be used include potassium citrate, sodium citrate, potassium succinate, sodium succinate, or mixtures thereof. When present, the burn control agent can be applied to the reconstituted plant material generally in an amount greater than about 0.1% by weight, such as in an amount greater than about 0.5% by weight, such as in an amount greater than about 1% by weight and generally less than about 5% by weight, such as less than about 4% by weight, such as less than about 3% by weight, such as less than about 2% by weight.

The reconstituted plant material of the present disclosure may also optionally contain a filler. The filler can comprise particles incorporated into the reconstituted web material for any desired purpose, such as for facilitating formation of the reconstituted plant material and/or for affecting the appearance of the material. Filler particles that may be incorporated into the reconstituted web material can be made from calcium carbonate, magnesium oxide, kaolin clay, bentonite, or mixtures thereof. Filler particles can optionally be incorporated into the reconstituted web material in an amount greater than about 1% by weight, such as in an amount greater than about 3% by weight, such as in an amount greater than about 5% by weight, such as in an amount greater than about 10% by weight, and generally in an amount less than about 30% by weight, such as in an amount less than about 25% by weight, such as in an amount less than about 20% by weight, such as in an amount less than about 15% by weight, such as in an amount less than about 10% by weight, such as in an amount less than about 8% by weight.

Once the reconstituted plant material has been formed into a fibrous substrate as described above, the material can be used as an aerosol generating material for use in any suitable smoking article or in a device that heats but does not combust the material. In one embodiment, the reconstituted plant material can first be formed into a loose filler material by being fed through a shredding or cutting process. For instance, the loose filler material can be in the forms of a strip, strips, shreds, or mixtures thereof. The loose filler material can then be packed into any suitable aerosol generating device or smoking article.

For instance, referring to FIG. 1, one embodiment of a reconstituted plant material filler 10 made in accordance with the present disclosure is shown. As illustrated, the filler 10 is made from shreds or strips of material that form a loose filler material.

In one aspect, the reconstituted plant material can be formulated so that the material can be easy to cut and/or shred. In addition, the reconstituted plant material can be formulated so that the material does not shed particles or pieces of material when handled. For example, in one embodiment, in order to improve the cutting ability of the product, the amount of web building fibers contained in the reconstituted plant material can be minimized without compromising the strength of the material. In addition, smaller fibers, such as hardwood fibers, can be used instead of or in addition to longer fibers, such as softwood fibers. The intensity of refining of the fibers can also be increased in order to improve the cutting ability and to prevent particle loss during handling. The cutting properties can also be improved by decreasing the basis weight of the material.

The reconstituted plant material of the present disclosure produces an aerosol or smoke that has a very neutral and pleasing taste. An aerosol generated by the material has no harsh components. In fact, the presence of the extracted cocoa husk can, in some embodiments, produce a roasted cocoa smell and/or taste. Of particular advantage, the reconstituted plant material of the present disclosure is nicotine free and thus can be used to produce a nicotine-free smoking article or a nicotine-free aerosol generating product or can be used to control nicotine delivery in the above products.

In one embodiment, for instance, the reconstituted plant material of the present disclosure can be combined with a tobacco material to form an aerosol generating material that produces an aerosol or smoke with less nicotine in comparison to an aerosol generated by the tobacco material by itself. For example, the reconstituted plant material of the present disclosure can be combined with any suitable tobacco material in an amount sufficient to produce an aerosol generating material that produces an aerosol containing a controlled and desirable amount. For example, in one embodiment, the nicotine levels in the reconstituted plant material can be less than about 0.5% by weight. In an alternative embodiment, nicotine levels can be greater than about 0.5% by weight of the reconstituted plant material.

The tobacco material blended with the reconstituted plant material of the present disclosure can comprise, for instance, cut leaf tobacco, a reconstituted tobacco material, or mixtures thereof. In one embodiment, the reconstituted plant material of the present disclosure can be in the form of a loose filler material that is homogenously blended with a tobacco material for forming an aerosol generating material with reduced nicotine deliveries and a desirable taste and smell. The aerosol generating material, for instance, may contain the reconstituted plant material of the present disclosure in an amount greater than about 5% by weight, such as in an amount greater than about 10% by weight, such as in an amount greater than about 20% by weight, such as in an amount greater than about 30% by weight, such as in an amount greater than about 40% by weight, such as in an amount greater than about 50% by weight, such as in an amount greater than about 60% by weight, such as in an amount greater than about 70% by weight, such as in an amount greater than about 80% by weight. The reconstituted plant material of the present disclosure can be combined with a tobacco material such that the resulting aerosol generating material may contain the reconstituted plant material in an amount less than about 90% by weight, such as in an amount less than about 80% by weight, such as in an amount less than about 70% by weight, such as in an amount less than about 60% by weight, such as in an amount less than about 50% by weight, such as in an amount less than about 40% by weight, such as in an amount less than about 30% by weight. For example, in one embodiment, the aerosol generating material may contain the reconstituted plant material of the present disclosure in an amount from about 5% to about 30% by weight, such as in an amount from about 10% to about 20% by weight. In an alternative embodiment, greater amounts of the reconstituted plant material may be incorporated into the aerosol generating material. In this embodiment, the reconstituted plant material may be contained in the aerosol generating material in an amount from about 30% to about 80% by weight, such as in an amount from about 40% to about 60% by weight. The above weight percentages are based upon the total weight of the aerosol generating material. The remaining portion of the aerosol generating material can be supplied exclusively by a tobacco filler.

Similar to controlling nicotine levels in tobacco, the reconstituted cocoa husk material of the present disclosure can also be used to control the levels of one or more cannabinoids contained in a *cannabis* material. For instance, the reconstituted plant material of the present disclosure can also be blended with a *cannabis* material, which may comprise dried flowers, dried buds, dried leaves, a reconstituted *cannabis* material, or mixtures thereof. For example, in one embodiment, the reconstituted cocoa husk material of the present disclosure can be in the form of a loose filler that is homogeneously blended with the *cannabis* material to form an aerosol generating material with controlled levels of cannabinoids and a desirable taste and smell. The aerosol generating material, for instance, may contain the reconstituted cocoa husk material of the present disclosure in an amount generally greater than about 5% by weight, such as in an amount greater than about 10% by weight, such as in an amount greater than about 20% by weight, such as in an amount greater than about 30% by weight, such as in an amount greater than about 40% by weight, such as in an amount greater than about 50% by weight, such as in an amount greater than about 60% by weight, and generally in an amount less than about 90% by weight, such as in an amount less than about 80% by weight, such as in an amount less than about 70% by weight, such as in an amount less than about 50% by weight, such as in an amount less than about 30% by weight. Similarly, the aerosol generating material can contain the *cannabis* filler or material in an amount greater than about 5% by weight, such as in an amount greater than about 10% by weight, such as in an amount greater than about 20% by weight, such as in an amount greater than about 30% by weight, such as in an amount greater than about 40% by weight, such as in an amount greater than about 50% by weight, such as in an amount greater than about 60% by weight, and generally in an amount less than about 90% by weight, such as in an amount less than about 80% by weight, such as in an amount less than about 70% by weight, such as in an amount less than about 60% by weight, such as in an amount less than about 50% by weight.

In addition to being combined with tobacco and/or *cannabis* filler materials, it should be understood that the reconstituted plant material of the present disclosure can be combined with any suitable aerosol generating filler. For instance, the reconstituted plant material of the present disclosure can also be combined with herbal plants, botanical plants, and the like. Examples of herbal plants, botanical plants, and trees, include cocoa tree, coffee tree or coffee bean, tea tree or tea leaf, vine, ginger, ginkgo, camomile, tomato, ivy, mate, rooibos, cucumber, mint, a cereal such as wheat, barley or rye, or other trees such as broadleaved or resinous trees, and the like, as well as combinations thereof.

In addition to or instead of being combined with other aerosol generating fillers, the reconstituted plant material of the present disclosure is well suited to receiving aerosol delivery agents. The reconstituted plant material, for instance, is highly absorbable and can contain up to 50% by weight of topical additives. In this regard, the reconstituted plant material of the present disclosure is also well suited to acting as a carrier for various different aerosol delivery compositions. Each aerosol delivery composition, for instance, can contain one or more aerosol delivery agents. The reconstituted plant material of the present disclosure can deliver the one or more aerosol delivery agents to a user through an aerosol generated by the material in controlled amounts and in a uniform and consistent manner.

Aerosol delivery compositions that can applied to the reconstituted plant material of the present disclosure include solutions, suspensions, oils, and the like. Solutions and suspensions, for instance, can be applied to the reconstituted plant material and later dried leaving behind a solid residue within the fiber substrate.

In one embodiment, an aerosol delivery composition may be obtained by extracting a plant substance from a plant for application to the reconstituted plant material. Additionally or alternatively, the present disclosure may include a step for isolating at least one compound from a plant substance, concentrating a plant substance, or even a purifying or eliminating a compound from a plant substance, in order to obtain a modified plant substance to be applied to the reconstituted material. While optional, such a process may result in the transformation of an original raw plant substance into a modified plant substance, whether in the form of dry extracts, liquid extract, a liquor or an isolated substance, based upon the desired end properties of the plant substance to be applied to the reconstituted material. Of course, while the plant substance may be an original plant substance or a modified plant substance, in one embodiment, the plant substance is applied to the reconstituted plant material without undergoing any further processing after extraction. Furthermore, while the aerosol delivery composition has been described as being extracted from a plant, it should be understood that synthetic or naturally occurring aerosol delivery compositions (e.g. without needing to be extracted) may also be used.

Examples of aerosol delivery agents that may be contained in the aerosol delivery composition include, or may be an extract of, (in addition to nicotine) sugars, licorice extracts, menthol, honey, coffee, maple syrup, tobacco, botanical extracts, plant extracts, tea, fruit extracts, flavorings such as clove, anise, cinnamon, sandalwood, geranium, rose oil, vanilla, caramel, cocoa, lemon oil, *cassia*, spearmint, fennel, or ginger, fragrances or aromas such as cocoa, vanilla, and caramel, medicinal plants, vegetables, spices, roots, berries, bar, seeks, essential oils and extracts thereof, such as anise oil, clove oil, carvone and the like, artificial flavoring and fragrance materials such as vanillin, and mixtures thereof. The extracts applied to the reconstituted plant material can be water soluble or oil soluble. Thus, various different carrier liquids can be used to apply the aerosol delivery agents to the reconstituted plant material.

In one embodiment, the reconstituted plant material of the present disclosure can be used as a carrier for components obtained from *cannabis*. Various chemicals and compounds contained in *cannabis* are becoming more and more popular drugs for pain relief in lieu of conventional pain relief medicines, such as opioids. *Cannabis*, for instance, contains various cannabinoids that can be used for pain relief. Inhaling an aerosol created by *cannabis* is the most common and least expensive method for delivering drugs contained in *cannabis* to a user. Unfortunately, however, merely inhaling aerosol generated from dried *cannabis* buds or leaves can lead to non-uniform deliveries of the pain relief drugs contained in the plant. Deliveries of the cannabinoids, for instance, can vary dramatically depending upon the particular plant and the particular plant parts being used to generate the aerosol. In addition, cannabinoid deliveries can vary dramatically based upon other factors such as the packing density of the material, the particular type of aerosol generating device or smoking article used to produce an aerosol, and the like. In addition, aerosols created from *cannabis* plant can contain irritants and produce a relatively harsh aerosol or smoke. The reconstituted plant material of the present disclosure, however, can be used to deliver cannabinoids in an aerosol generated from the material without any of the above drawbacks and deficiencies. For instance, the aerosol generated from the reconstituted plant material of the present disclosure is non-irritating, does not contain harsh components, and has a neutral taste. In addition, applying cannabinoids topically to the reconstituted plant material allows for uniform and consistent deliveries of the cannabinoids when contained in an aerosol generated by the reconstituted plant material and inhaled.

Cannabinoids that can be incorporated into the reconstituted plant material of the present disclosure include cannabidiol (CBD) and tetrahydrocannabinol (THC). THC contained in *cannabis* acts on specific receptors in the brain which lead to a feeling of euphoria and a relaxed state. CBD, on the other hand, also interacts with pain receptors in the brain but does not create the same euphoric feeling caused by THC. In accordance with the present disclosure, in one embodiment, THC can be applied to the reconstituted plant material of the present disclosure, CBD can be applied to the reconstituted plant material or, alternatively, both THC and CBD can be applied to the reconstituted plant material.

In addition to THC and CBD, various other cannabinoids can also be incorporated into an aerosol delivery composition and applied to the reconstituted plant material in accordance with the present disclosure. For instance, other cannabinoids contained in *cannabis* include cannabichromene, cannabinol, cannabigerol, tetrahydrocannabivarin, cannabidivarin, cannabidiolic acid, other cannabidiol derivatives, and other tetrahydrocannabinol derivatives. The above cannabinoids can be used singularly or in any combination and applied to the reconstituted plant material.

The cannabinoids described above can be applied to the reconstituted plant material using various different methods. For instance, in one embodiment, the cannabinoid, such as CBD, can be formulated into an aqueous suspension or can be dissolved in a solvent, such as a fat or oil. For example, a *cannabis* oil extract may be obtained from raw *cannabis* plants. The oil extract may contain THC alone, CBD alone, or a combination of THC and CBD. The oil extract can be applied to the reconstituted plant material so that an aerosol generated by the material contains controlled amounts of the cannabinoids. In addition to containing controlled amounts of the cannabinoids, the reconstituted plant material can also be designed to provide uniform deliveries of the cannabinoids in the aerosol generated from the material.

Another component that can be added to the reconstituted plant material are various flavorants, especially terpenes. A terpene or a blend of terpenes, for instance, can be used to develop desirable aromas and indicate to the user the quality of the product. One or more terpenes can also improve the sensory reaction to inhaling an aerosol created by the reconstituted material.

Various different terpenes can be applied to the reconstituted plant material. Such terpenes include but are not limited to pinene, humulene, b-caryophyllene, isopulegol, guaiol, nerylacetate, neomenthylacetate, limonene, menthone, dihydrojasmone, terpinolene, menthol, phellandrene, terpinene, geranylacetate, ocimene, myrcene, 1,4-cineole, 3-carene, linalool, menthofuran, perillyalcohol, pinane, neomenthylaceta, alpha-bisabolol, borneol, camphene, camphor, caryophyllene oxide, alpha-cedrene, beta-eudesmol, fenchol, geraniol, isoborneol, nerol, sabinene, alpha-terpineol, and mixtures thereof.

In one embodiment, various different terpenes can be blended together in order to mimic the ratios of terpenes found in natural smokable plants. For instance, from about 2 to about 12 terpenes can be blended together and applied to the reconstituted plant material. Each terpene can be applied to the reconstituted plant material in an amount greater than about 0.001% by weight and generally less than about 5% by weight. For instance, each terpene can be applied in an amount from about 0.01% by weight to about 1.5% by weight. For instance, each terpene can be applied in an amount from about 0.1% to about 1.1% by weight.

Exemplary blends of terpenes include alpha-pinene, beta-caryophyllene, and beta-pinene; alpha-humulene, alpha-pinene, beta-caryophyllene, beta-pinene, and guaiol; beta-caryophyllene, beta-pinene, and d-limonene; beta-caryophyllene, beta-pinene, and nerolidol; beta-caryophyllene, beta-pinene, d-limonene, and terpinolene; alpha-bisabolol, alpha-pinene, beta-caryophyllene, beta-myrcene, beta-pinena, and d-limonene; beta-caryophyllene, beta-pinena, and p-cymene; alpha-humulene, beta-caryophyllene, beta-pinene, d-limonene, linalool, and nerolidol; beta-caryophyllene and beta-pinene; beta-caryophyllene, beta-myrcene, and terpinolene; alpha-pinene, beta-caryophyllene, beta-pinene, d-limonene; alpha-humulene, alpha-pinene, beta-caryophyllene, beta-myrcene, beta-pinena, d-limonene, and guaiol.

Aerosol delivery compositions containing one or more aerosol delivery agents as described above can be applied to the reconstituted plant material using any suitable method or technique. For instance, the aerosol delivery composition can be sprayed or coated onto the fiber substrate in any suitable manner.

Reconstituted plant materials made in accordance with the present disclosure have excellent mechanical characteristics and have a very desirable and aesthetic appearance. In general, the reconstituted plant material has a basis weight of greater than about 40 gsm, such as greater than about 45 gsm, such as greater than about 55 gsm. The basis weight of the reconstituted plant material is generally less than about 120 gsm, such as less than about 100 gsm, such as less than about 85 gsm.

In one embodiment, the reconstituted plant material of the present disclosure can be formed into a loose filler using various methods, such as extrusion or through cutting and/or shredding the reconstituted material. Filler material made in accordance with the present disclosure can have a filling power of greater than about 4 $cm^3/g$, such as greater than about 5 $cm^3/g$, such as greater than about 6 $cm^3/g$, and generally less than about 10 $cm^3/g$, such as less than about 8 $cm^3/g$. The reconstituted plant material can have excellent burn properties. For instance, the reconstituted plant material can have a static burn rate of greater than about 4 mm/mm, such as greater than about 5 mm/mm, and generally less than about 8 mm/mm, such as less than about 7 mm/mm.

The reconstituted plant material of the present disclosure has excellent taste characteristics while also being free from nicotine and producing relatively low amounts of tar, especially in comparison to conventional tobacco materials. Unexpectedly, it was also discovered that the reconstituted cocoa husk material of the present disclosure does not produce a "papery" taste, even though the material can contain significant amounts of cellulose fibers, such as softwood fibers. Although unknown, it is believed that the extracted cocoa fibers mask or otherwise suppress any paper-like taste when the material is burned or otherwise heated. This discovery is surprising and completely unexpected.

Consequently, an aerosol generating material incorporating the reconstituted plant material of the present disclosure can be used in all different types of aerosol generating products. In one embodiment, for instance, the aerosol generating material of the present disclosure can be formed into a smokable rod and surrounded by an outer wrapper. The smoking article, or cigarette, can include a filter located at one end of the smoking article. However, because of the neutral and mild characteristics of an aerosol produced from the reconstituted plant material and because the reconstituted plant material has no harsh components and is low in nicotine and tar, cigarettes can be made according to the present disclosure can be filterless.

In one embodiment, the reconstituted plant material is formed on a paper forming machine and is in the form of a sheet. The sheet can then be cut into strips and fed to a rotating or agitated drum. When in the drum, the reconstituted plant material can be mixed with one or more humectants and a casing. The casing can contain various different flavorants or mainstream smoke enhancing elements. For instance, the casing may contain licorice, corn syrup, and/or sugar. From the drum, the reconstituted plant material can undergo a cutting or grinding process in order to reduce the material to a desired particle size. The cut reconstituted plant material is sometimes referred to as cut rag. Once cut to a desired size, various different aerosol delivery agents or flavorants can be applied to the reconstituted plant material. For instance, one or more terpenes can be applied to the reconstituted plant material and/or one or more cannabinoids, such as CBD and/or THC. Once the aerosol delivery agents are applied to the reconstituted plant material, the reconstituted plant material can be packaged and shipped for use in any suitable form. In one aspect, the reconstituted plant material can be fed to a cigarette making machine for forming the reconstituted plant material into rod-like elements. Alternatively, the material can be packaged in loose form and used as a filling for roll-your-own products, heat but not burn products, or snuff.

In addition to cigarettes, aerosol generating materials made according to the present disclosure can also include cigars and cigarillos.

The reconstituted plant material of the present disclosure can also be used to produce a snuff product. The snuff product can be a dry product or can contain substantial amounts of moisture.

When producing a smokeless blend product (e.g. snuff), the product can be made exclusively from the reconstituted plant material of the present disclosure or can be formed from the reconstituted plant material of the present disclosure blended with other filler materials. When the reconstituted plant material of the present disclosure is used to form a smokeless blend, the amount of web building fibers contained in the product may be reduced. For instance, the amount of web building fibers can be less than about 5% by weight, such as less than about 3% by weight. In one aspect, the reconstituted plant material may not contain any web building fibers. In another embodiment, the reconstituted plant material may contain from about 5% to about 50% by weight web building fibers.

In order to form a smokeless blend product, the reconstituted plant material of the present disclosure is ground or cut to a desired size. For instance, the particle size can be relatively small or can be made into strips depending upon the end use application. In one aspect, for instance, the material is cut or ground so as to have an average particle size of greater than about 50 microns, such as greater than about 100 microns, and generally less than about 3 mm, such as less than about 2 mm. Alternatively, the material can be ground into a powder or a granular material wherein the average particle size is less than about 100 microns.

If desired, the reconstituted plant material can be subjected to a heat treatment. The heat treatment may provide the material with texture and color and enhance the natural flavors. After an optional heat treatment step, additives such as pH-regulators and flavorings can be added to the mixture. When forming a moist smokeless product, water can be added to the product such that the water content is greater than about 10% by weight, such as greater than about 20% by weight, such as greater than about 30% by weight, such as greater than about 40% by weight, and generally less than about 60% by weight, such as less than about 50% by weight. If desired, one or more moisture agents can be added to the product that facilitates the moisture retaining properties of the blend. In one aspect, for instance, sodium chloride and/or sodium carbonate can be added to the reconstituted plant material Alternatively, the reconstituted plant material can be used to produce a dry smokeless blend, such as a dry oral snuff. In order to produce a dry oral snuff, the material is ground into a powder to which other ingredients such as flavors are added.

In one aspect, the smokeless reconstituted *cannabis* material can be placed in an oral pouch that is intended for use in the oral cavity, such as by placing the pouch between the upper and lower gum of the lip or cheek. The oral pouched product may have an oblong shape, such as a rectangular shape. The total weight of the oral pouch can generally be in the range of from about 0.1 g to about 2.5 g, such as from about 0.2 g to about 0.8 g. The pouch can be made of any suitable saliva-permeable pouch material, such as a nonwoven. A binder may be included in the pouch to facilitate sealing of the material by ultrasonic welding. The binder, for instance, can be an acrylate polymer. In one aspect, the pouch can be formed from a nonwoven material containing regenerated cellulose fibers, such as viscose rayon staple fibers and a binder. If desired, the pouch material may also contain additional flavoring agents and/or colorants.

In one embodiment, smoking articles made according to the present disclosure can also have reduced ignition propensity characteristics. For instance, an outer wrapper of the smoking article can include a plurality of discrete reduced ignition areas spaced in the axial direction of the smoking article. For instance, in one embodiment, the discrete reduced ignition areas may be in the form of circular bands. The bands can have a width so that oxygen is limited to the burning coal for a sufficient length or period of time to extinguish the coal if the smoking article were left in a static burn condition. The bands, for instance, can have a width of generally greater than about 3 mm, such as greater than about 4 mm, such as greater than about 5 mm, and generally less than about 10 mm, such as less than about 8 mm, such as less than about 7 mm.

The spacing between the reduced ignition areas can also vary depending upon a number of variables. The spacing should not be so great that the cigarette burns for a sufficient length of time to ignite a substrate before the coal burns into a reduced ignition area. The spacing also affects the thermal inertia of the burning coal, or the ability of the coal to burn through the reduced ignition areas without self-extinguishing. In general, the band spacing should be greater than about 5 mm, such as greater than about 10 mm, such as greater than about 15 mm, and generally less than about 50 mm, such as less than about 40 mm, such as less than about 30 mm. Each smoking article can contain from about 1 to about 3 bands.

In general, any suitable ignition reducing composition can be applied to the outer wrapper of the smoking article. In one embodiment, for instance, the ignition reducing composition contains a film-forming material. For example, film-forming materials that can be used in accordance with the present invention include alginates, guar gum, pectin, polyvinyl alcohol, polyvinyl acetate, cellulose derivatives such as ethyl cellulose, methyl cellulose, and carboxymethyl cellulose, starch, starch derivatives, and the like.

In one particular embodiment, the film-forming material may comprise an alginate, alone or in combination with starch. In general, an alginate is a derivative of an acidic polysaccaride or gum which occurs as the insoluble mixed calcium, sodium, potassium and magnesium salt in the Phaeophyceae brown seaweeds. Generally speaking, these derivatives are calcium, sodium, potassium, and/or magnesium salts of high molecular weight polysaccharides composed of varying proportions of D-mannuronic acid and L-guluronic acid. Exemplary salts or derivatives of alginic acid include ammonium alginate, potassium alginate, sodium alginate, propylene glycol alginate, and/or mixtures thereof.

In one embodiment, a relatively low molecular weight alginate may be used. For example, the alginates may have a viscosity of less than about 500 cP when contained in a 3% by weight aqueous solution at 25° C. More particularly, the alginates may have a viscosity of less than 250 cP at the above conditions, particularly less than 100 cP, and in one embodiment at a viscosity of about 20-60 cP. As used herein, viscosity is determined by a Brookfield LVF Viscometer with a suitable spindle according to the viscosity. At the above lower viscosity levels, alginate compositions can be formed at a higher solids content, but yet at a low enough solution viscosity to permit the application of the composition to a paper wrapper using conventional techniques. For example, the solids content of an alginate solution made in accordance with the present invention can be greater than about 6%, particularly greater than about 10%, and more particularly from about 10% to about 20% by weight.

At the above solids levels, alginate compositions used in accordance with the present invention can have a solution viscosity of greater than about 250 cP, particularly greater than about 500 cP, more particularly greater than about 800 cP, and in one embodiment at a viscosity of greater than about 1,000 cP at 25° C. In general, the solution viscosity of the alginate film-forming composition can be adjusted depending upon the manner in which the composition is being applied to the wrapper. For instance, the solution viscosity of the composition can be adjusted depending upon whether or not the composition is being sprayed onto the wrapper or printed onto the wrapper.

In other embodiments, it should also be understood that depending upon the application a relatively high molecular weight alginate may be used. For example, the alginate may have a viscosity of greater than about 500 cP when contained in a 3% by weight aqueous solution at 25° C.

In addition to the film-forming material, the reduced ignition composition applied to the wrapper can contain various other ingredients. For instance, in one embodiment, a filler can be contained within the composition. The filler can be, for instance, calcium carbonate, calcium chloride, calcium lactate, calcium gluconate, and the like. In addition to calcium compounds, other various particles may be used including magnesium compounds such as magnesium oxide, clay particles, and the like.

The ignition reducing composition, in one embodiment, can be water based. In particular, the ignition reducing composition may comprise an aqueous dispersion or aqueous solution. Alternatively, the ignition reducing composition prior to being applied to the paper wrapper may comprise a non-aqueous solution or dispersion. In this embodiment, for instance, an alcohol may be present for applying the composition to the wrapper.

As opposed to a film-forming composition, the ignition reducing composition may also comprise a cellulose slurry (a type of dispersion). As used herein, a slurry containing papermaking materials is not a film-forming composition. The cellulose slurry applied to the paper substrate may comprise fibrous cellulose, one or more fillers, and/or cellulose particles. As used herein, cellulose fibers and cellulose particles are to be differentiated from derivatized cellulose such as carboxymethyl cellulose. Cellulose fibers and cellulose particles, for instance, are not water soluble. In one embodiment, the cellulose slurry applied to the wrapper may comprise microcrystalline cellulose.

Once the ignition reducing composition is formulated, the composition can be applied to a wrapper in discrete areas. The manner in which the composition is applied to the wrapper can vary. For example, the composition can be sprayed, brushed, applied with a moving orifice, or printed onto the wrapper. To form a treated area, the composition can be applied in a single pass or in a multiple pass operation. For instance, the composition can be applied to the wrapper in successive steps in order to form areas on the wrapper having reduced ignition proclivity. In general, during a multiple pass process, the treated areas can be formed by applying the composition during from about 2 to about 8 passes.

The amount of reduced ignition composition applied to the wrapper can also vary. For instance, the composition can be applied to the wrapper in an amount less than about 15% by weight, such as less than about 10% by weight, such as less than about 8% by weight. In general, the composition is applied in an amount greater than 1% by weight based upon the weight of the composition within the reduced ignition areas.

As used herein, the above weight percentages are based on the area treated with the chemical components. In other words, the weight percentages above for the reduced ignition composition is the amount applied within the treated areas as opposed to the total amount applied over the entire surface of the wrapper.

Through the process of the present disclosure, reduced ignition areas can be produced having a relatively high permeability while also having a relatively low diffusivity. For instance, the reduced ignition areas can have a permeability greater than 10 CORESTA while still being capable of producing smoking articles that pass ASTM Test E2187-09 at least 75% of the time.

In general, the reduced ignition areas have a diffusivity that is relatively low. The diffusivity can be measured at room temperature (23° C.). In general, the diffusivity at 23° C. of the reduced ignition areas is less than about 0.5 cm/s, such as less than 0.4 cm/s, such as less than 0.3 cm/s. In one embodiment, the reduced ignition areas may have a diffusivity of greater than about 0.05 cm/s, such as greater than about 0.15 cm/s, such as greater than 0.16 cm/s, such as greater than 0.17 cm/s, while still having the desired reduced ignition proclivity characteristics. Diffusivity is measured using a Sodium $CO_2$ diffusivity tester.

In addition to being incorporated into smoking articles, the aerosol generating material of the present disclosure can also be packaged and sold in various other forms to consumers. For instance, in one embodiment, the aerosol generating material can be packaged and sold as a filler material in the form of strips or shreds. The filler material can then be used in pipes, as a filler in a roll-your-own smoking article, or can be used in an aerosol generating device that heats but does not combust the material.

The present disclosure may be better understood with reference to the following examples.

EXAMPLES

The following test methods are used to not only define the various parameters but also were used in obtaining the results in the examples below.

Tests & Methods

Filling Power and Equilibrium Moisture Content (EMC)

The sample of filler material is conditioned according to ISO 3402 (22° C.+/−1° C., 60%+/−3% R.H., during min. 48 hrs). After conditioning, the material is unfolded (if needed) and cut into cut rag (equipment: BUROMA disc cutter; width: 0.7 mm).

To perform filling power analysis, 14 g of cut filler (precision: +/−0.01 g) is placed into a Borgwaldt cylinder (DM4625 model; diameter=5.98 cm, height=10.8 cm). A weight of 2 kg is applied during 60 sec. When the piston is released, the height of the filler column is displayed and recorded (H, in cm).

The filling power of the sample (in cc/g) is calculated as: 2×H.

Equilibrium Moisture Content is measured according to the following method: The weight of an empty pan (made of glass) is measured, at a precision of +/−1 mg, and recorded (T).

The pan is then filled with cut filler (between 5 and 7 g) and the weight of the pan with cut filler is recorded (W1, precision+/−1 mg).

The pan with cut filler is then dried in a Hearson oven (Mark V), during 3 hrs (+/−5 min), at 100° C.

After drying, the pan is cooled in a dessicator during 15 min and its weight is measured (W2, precision+/−1 mg). Moisture of the sample (%) is calculated as:

$$\frac{W1-W2}{W1-T} \times 100$$

Water Solubles Content

The sample of filler is ground into powder (using a IKA or RETSCHE-MUHLE grinder; mesh size: 1 mm).

A glass fiber filter (DURIEUX filter Nr 28, diam.=55 mm) is placed in a stainless steel pan. The tare of the pan+filter is then weighed (T, precision+/−1 mg). A 5000 mg (+/−200 mg) sample of ground filler is placed in the pan and precisely weighed (W1, precision+/−1 mg).

The ground filler is gently sprayed with water and the cup is installed into a lab percolator (RENEKA LC). Extraction is performed three times according to the pre-defined percolation settings. After percolation, the sample is cautiously washed with water and the pan is dried in an electric oven for 16 hrs at 100° C.

After washing, the pan is cooled in a dessicator during 15 min and its weight is measured (W3, precision+/−1 mg).

Dry weight of the ground sample used for Water solubles test (W2) is calculated as: W2=W1×(100−H)/100.

Finally, the ratio of Water solubles (%) in the dry finished product is calculated as follows;

$$WS\ (\%) = 1,15 \times \left(\left(\frac{W2-(W3-T)}{W2}\right) \times 100\right) - 2,0$$

Cigarettes Making

The sample of filler is conditioned according to ISO 3402 (22° C.+/−1° C., 60%+/−3% R.H., during min. 48 hrs). After conditioning, the filler sheets are cut into shreds (equipment: BUROMA disc cutter; width: 0.7 mm). The cut material is sieved on a laboratory sieve (mesh size; 1 mm).

Empty cigarettes tubes are then filled with 100% cut filler, using a hand rolling machine from PRIVILEG. The weight of cut filler is adjusted to reach a Pressure Drop of 100+/−5 mm WG.

The empty tubes have the following characteristics:
tube weight=200±5 mg,
total length=84 mm, diameter=8.1±0.1 mm, tipping length=25 mm
acetate filter (denier=3.0Y/35000HK, length=15±0.5 mm, pressure drop=43±3 mm WG),
cigarette paper porosity=50 CU,
no filter ventilation.

Cigarettes are then sorted on a SODIMAT machine. The lot of cigarettes selected to perform smoke analyses have the following characteristics: filler weight:average target weight+/−10 mg, pressure drop: average target PD+/−3.5 mm WG.

Before performing smoke analyses, cigarettes are conditioned according to ISO 3402 (22° C.+/−1° C., 60%+/−3% R.H., during min. 48 hrs).

Analysis of Combustibility 10 cigarettes are positioned on a FILTRONA static burn rate machine. This machine has 10 cigarette holders and 10 individual chronometers.

Two cotton threads, 40 mm away from each other, are settled right over the 10 cigarettes. Each thread is connected to the chronometer.

The cigarettes are lit sequentially. For each cigarette, when the combustion cone cuts the front cotton line, the chronometer is automatically activated. Once the char line reaches the second cotton thread, the chronometer automatically stops thus giving the time necessary to burn 40 mm of the filler rod.

An average time (in seconds) is calculated from the 10 chronometers.

The average combustibility (in mm/min) is calculated as:

$$\frac{40 \times 60}{\text{Average time}}$$

Analysis of Tar, Nicotine, Water and CO in Smoke 2 sets of 20 cigarettes are smoked on a Borgwaldt RM20 kit machine, in standard ISO conditions (ISO 3308).

Nicotine and water in smoke (mg/cig) are measured by Gas Chromatography, according to standards ISO 10315 and ISO 10362-1.

Tar in smoke (mg/cig) is measured according to standard ISO 4387.

CO in smoke (mg/cig) is measured by Non-Dispersive Infra-Red (NDIR) method, according to standard ISO 8454.

Bursting Strength

Condition material during minimum 48 hours @ 60±2% relative humidity, 22±1° C.

Cut test samples at 60 mm diameter.

Measure the bursting strength using a bursting meter IDM according to the AFNOR Norm NFQ 03. 053.

Measurement on 4 samples of material to calculate an average value.

Cutting Fragility

Condition 50 g of material during minimum 48 hours @ 60±2% relative humidity, 22±1° C.

Cut leaflets into cut rag with disc cutter at 0.7 mm width.

Sieve cut material into a 0.8 mm sieve (Ø wire=0.5 mm) during 5 min

Weigh >0.8 mm material (M1) and <0.8 mm (M2) material with a precision of 0.01 g The fragility when cutting is: =M2/M1+M2)·100(%)

Handling Fragility

Weigh 20+/−0.5 g of >0.8 mm cut material (after cutting and sieving)

Sieve the material into a 0.8 mm sieve (Ø wire=0.5 mm) during 5 min

Weigh >0.8 mm material (M3) and <0.8 mm (M4) material with a precision of 0.01 g The fragility when handling is: =M4/(M3+M4)·100(%)

Example 1

A cocoa filler according to the present disclosure comprising fibres originating from cocoa (*Theobroma cacao*) tree was manufactured according to the following method: cocoa husks were ground using a knife mill so as to obtain particles about 1 mm in size. The ground husk material was then mixed with water at 70° C. for 45 minutes, in a husk/water ratio of 1/10. The mixture was then pressed so as to separate the aqueous part (cocoa husk fluid) from the insoluble part (cocoa husk fibres). The fibrous fraction was refined using disc refiners. After refining, delignified fibres originating from resinous trees (softwood fibers) were added to the refined fibre fraction in a ratio of delignified fibres/fibres according to the invention from cocoa tree of 40%/60% so as to manufacture reconstituted cocoa filler sheets. The cocoa filler sheets were then dried.

Cocoa filler material showed the following characteristics;

| | Method | Cocoa Filler 60% cocoa fibres from husk + 40% cellulose fibres |
|---|---|---|
| Dry basis weight (g/m$^2$) | NF Q03 019 | 53 |
| Thickness (μm) | NF Q03 017 | 191.2 |
| Flexural strength 7.5° Machine Direction MD (mN) | ISO 2493-1, 2011 | 21.6 |
| Flexural strength 7.5° Cross Direction CD (mN) | ISO 2493-1, 2011 | 21.6 |
| Flexural strength 15° MD (mN) | ISO 2493-1, 2011 | 36.6 |
| Flexural strength 15° CD (mN) | ISO 2493-1, 2011 | 36.6 |
| Tensile Strength MD (kN/m) | ISO 1924-2 | 0.91 |
| Tensile Strength CD (kN/m) | ISO 1924-2 | 0.91 |
| Deformation before rupture MD (%) | ISO 1924-2 | 1.4 |
| Deformation before rupture CD (%) | ISO 1924-2 | 1.4 |
| Bursting Strength (KPa) | ISO 2758 | 47.4 |
| Hot water solubles (%) | As Described Above | 2.9 |
| Filling value (at EMC 11.2%) | As Described Above | 9.7 |

Example 2

A cocoa filler according to the present disclosure comprising fibres originating from cocoa (*Theobroma cacao*) tree was manufactured according to the following method: cocoa husks were ground using a knife mill so as to obtain particles about 1 mm in size. The ground husk material was then mixed with water at 70° C. for 45 minutes, in a husk/water ratio of 1/10. The mixture was then pressed so as to separate the aqueous part (cocoa husk fluid) from the insoluble part (cocoa husk fibres). The fibrous fraction was refined using disc refiners. After refining, delignified fibres originating from resinous trees (softwood fibers) were added to the refined fibre fraction in a ratio of delignified fibres/fibres to cocoa husk fibers of 40%/60% so as to manufacture reconstituted cocoa filler sheets. The cocoa filler sheets were then dried. In parallel, the aqueous portion prepared as above, and originating from cocoa tree (coca husk fluid), also called "extracts" was concentrated in an evaporator to a solid concentration of 20% to be then coated or not on cocoa filler sheets by coating with a size press. Before being dried, various other substances are also added to the cocoa filler sheets by coating and/or spraying according to the table below:

| A | 97% Cocoa filler/3% Aroma 1 added by spraying |
|---|---|
| B | 97% Cocoa filler/3% Aroma 2 added by spraying |
| C | 97% Cocoa filler/3% Aroma 3 added by spraying |
| D | 97% Cocoa filler/3% Aroma 4 added by spraying |
| E | 97% Cocoa filler/3% Aroma 5 added by spraying |
| F | 72% Cocoa filler/Addition of 26% cocoa husk fluid from Example 2 + 2% inverted sugar |
| G | 59% Cocoa filler/Addition of 26% cocoa husk fluid from Example 2/15% vegetal glycerin |
| H | 97% Cocoa filler/3% Aroma 6 added by spraying |

Some cigarettes (A, B, C, D, E, F, H) were made for sensory evaluation purposes by a group of experts. A G sample was evaluated in a PAX 3 system for Heat-not-Burn application.

The following results were obtained:

| A | Nice aroma: citrus, floral, cannabis<br>Very little irritation |
|---|---|
| B | Very little aroma before cigarette lighting<br>Very close to basic cocoa filler |
| C | Very little aroma before cigarette lighting<br>Some mouth coating<br>Slightly irritant, close to tobacco experience |
| D | Very little aroma before cigarette lighting<br>Important mouth coating. Some acidity and floral notes.<br>Good level of irritation<br>Nice smoke odor |
| E | Very little aroma before cigarette lighting<br>Strong cannabis smoke odor and taste<br>Astringent |
| F | Stronger tobacco notes but higher irritation and some bitterness |
| G | Very strong but pleasant chocolate notes<br>Nice smoke volume<br>Long lasting taste<br>No irritation |
| H | Very little aroma before cigarette lighting<br>Very close to basic cocoa filler |

Example 3

A cocoa filler according to the present disclosure comprising fibres originating from cocoa (*Theobroma cacao*) tree was manufactured according to the following method: cocoa husks were ground using a knife mill so as to obtain particles about 1 mm in size. The ground husk material was then mixed with water at 70° C. for 45 Minutes, in a husk/water ratio of 1/10. The mixture was then pressed so as to separate the aqueous part (cocoa husk fluid) from the insoluble part (cocoa husk fibres). The fibrous fraction was refined using disc refiners. After refining; delignified fibres originating from resinous trees (softwood fibers) were added to the refined fibre fraction in a ratio of delignified fibres/fibres to cocoa tree of 40%/60% so as to manufacture reconstituted cocoa filler sheets. The cocoa filler sheets were then dried.

Tobacco extract corning from Tobacco material prepared as above in order to use aqueous part (tobacco fluid), also called tobacco "extracts". Those extracts were then added to the cocoa filler sheets by coating. Some reconstituted tobacco material was also manufactured according to the same methodology for the purpose of demonstration The following samples were made:

| A | 55% Cocoa filler/30% Tobacco extract/15% glycerin |
|---|---|
| B | 63% Cocoa filler/22% Tobacco extract/15% glycerin |
| D | 60% Cocoa filler/40% Tobacco extract |
| E | Control: 60% Tobacco fibers/40% Tobacco extract |
| F | Control: 55% Tobacco fibers/30% Tobacco extract/15% glycerin |

Sensory Evaluation

Sample A was compared to Sample F in Heat-not-Burn device (PAX3). No significant difference. Cocoa filler is neutral. It can replace tobacco fibers.

Sample D was compared to Sample E in conventional cigarettes conditions. No significant difference. Cocoa filler is neutral. It can replace tobacco fibers.

Sample A was compared to Sample Sin Heat-not-Burn device. As expected, tobacco notes and nicotine impact is lower on sample B.

Example 4

A cocoa and tobacco filler according to the present disclosure comprising fibres originating from cocoa (*Theo-

*broma cacao*) tree and Tobacco (*Nicotania tabcum*) plant was manufactured according to the following method: cocoa husks were ground using a knife mill so as to obtain particles about 1 mm in size. The ground husk material was then mixed with water at 70° C. for 45 minutes, in a husk/water ratio of 1/10. The mixture was then pressed so as to separate the aqueous part (cocoa husk fluid) from the insoluble part (cocoa husk fibres). The fibrous fraction was refined using disc refiners. After refining, delignified fibres originating from resinous trees and tobacco fibres prepared as above were added to the refined fibre fraction in a ratio of delignified fibres/tobacco fibres/cocoa fibres of 20%/60%/20% so as to manufacture cocoa and tobacco filler sheets. The cocoa and tobacco filler sheets were then dried.

In parallel, the aqueous portion prepared as above, and originating from Tobacco plant (tobacco fluid), also called tobacco "extracts" was concentrated in an evaporator to a solid concentration of 50% to be then coated or not on the cocoa and tobacco filler sheet by coating with a size-press and later dried. Some reconstituted tobacco material were also manufactured according to the same methodology for the purpose of demonstration.

The following samples were made:

| | |
|---|---|
| C | 55% Cocoa&tobacco filler + 30% Tobacco extract + 15% glycerin |
| F | Control - 55% Tobacco fibers + 30% Tobacco extract + 15% glycerin |

Sensory Evaluation

Sample C was compared to Sample F in Heat-not-Burn device (PAX3). No significant difference. Cocoa filler is neutral and can replace tobacco fibers.

Example 5

A cocoa filler according to the present disclosure comprising fibres originating from cocoa (*Theobroma cacao*) tree was manufactured according to the following method: cocoa husks were around using a knife mill so as to obtain particles about 1 mm in size. The ground husk material was then mixed with water at 70° C. for 45 minutes, in a husk/water ratio of 1/10. The mixture was then pressed so as to separate the aqueous part (cocoa husk fluid) from the insoluble part (cocoa husk fibres). The fibrous fraction was refined using disc refiners. After refining, delignified fibres originating from resinous trees (softwood fibers) were added to the refined fibre fraction in a ratio of delignified fibres/cocoa husk fibres of 40%/60% so as to manufacture reconstituted cocoa filler sheets. The cocoa filler sheets were then dried.

In parallel, the aqueous portion prepared as above, and originating from hemp (*Cannabis* spp.) plant (hemp fund), also called hemp "extracts" was concentrated in an evaporator to a solid concentration of 50% to be then coated on cocoa filler sheet by coating with a size-press and later dried.

Samples were made as follows:

| | |
|---|---|
| C | 67% Cocoa filler + 33% Hemp extract |
| D | 57% Cocoa filler + 28% Hemp extract + 15% glycerin |

Sensory Evaluation

Sample C was evaluated in conventional cigarette conditions. Nice smoke volume, good combustion and smell. No irritation. Little bitterness. Good Hemp notes—no Cocoa notes. Cocoa fibres are neutral, Sample D was compared in Heat-not-Burn device. Very good smoke volume. Distinctive Hemp/*cannabis* flavors with no cocoa notes. No irritation. Very pleasant. Cocoa fibres are neutral.

Example 6

The following samples were formulated and tested in order to improve the cutting ability of the product, to decrease bursting resistance, and/or to decrease particle loss during handling.

The following samples were formulated and tested for various properties. Sample Nos. 1 through 7 were produced in a laboratory environment on a small scale. Sample No. 8, however, was produced on commercial papermaking machinery. Sample Nos. 1 and 8 both contain cocoa shells and softwood fibers at a weight ratio of 100:33. Sample Nos. 2 and 4 only contain hardwood fibers, while Sample No. 4 further includes glycerin and cocoa extracts. Sample Nos. 3 and 5 both contain reduced levels of softwood fibers, while Sample No. 5 contains glycerin and cocoa extracts. In Sample Nos. 6 and 7, a combination of softwood and hardwood fibers was used.

| Sample No. | 1 | 2 | 3 | 4 | 5 | 6 | 7 | 8 |
|---|---|---|---|---|---|---|---|---|
| Raw materials | | | | | | | | |
| Cacao shells (%) | 67 | 67 | 80 | 67 | 80 | 67 | 67 | 67 |
| Softwood (%) | 33 | 0 | 20 | 0 | 20 | 18 | 18 | 33 |
| Hardwood (%) | 0 | 33 | 0 | 33 | 0 | 15 | 15 | 0 |
| Additives (% based on uncoated sheet weight) | | | | | | | | |
| Glycerin (%) | 0 | 0 | 0 | 5 | 5 | 5 | 5 | 0 |
| Cocoa extracts (%) | — | — | — | 19 | 23 | 19 | 19 | — |
| Theoretical recipe of the final product | | | | | | | | |
| Cocoa content (%) | 55 | 55 | 69 | 43 | 52 | 43 | 43 | 55 |
| Cellulose content (%) | 41 | 41 | 26 | 32 | 19 | 32 | 32 | 41 |
| Total extracts (%) | 4 | 4 | 5 | 25 | 29 | 25 | 25 | 4 |
| Other parameters: | | | | | | | | |
| Uncoated sheet basic weight (g/m$^2$) | 70 | 70 | 70 | 70 | 70 | 78 | 66 | 73.72 |

-continued

| Sample No. | 1 | 2 | 3 | 4 | 5 | 6 | 7 | 8 |
|---|---|---|---|---|---|---|---|---|
| Coated sheet basic weight (g/m²) | — | — | — | 93 | 90 | 98 | 83 | — |
| Refining degree (° SR) | 78 | 87 | 81 | 87 | 81 | 78 | 78 | 50 |
| Results | | | | | | | | |
| Bursting resistance (KPa) | 155.12 | 79.24 | 87.58 | 101.72 | 113.89 | 166.22 | 149.71 | 89.72 |
| Mini Filling power (cm³/g) | 10 | 9.9 | 10.1 | 8.7 | 8.1 | 8.9 | 8.6 | 9.7 |
| Cutting fragility (% of dust) | 0.90 | 0.30 | 0.40 | 0.20 | 0.80 | 0.60 | 0.60 | 1.40 |
| Handling fragility (% of dust) | 1.70 | 0.80 | 0.80 | 0.80 | 0.90 | 0.70 | 0.80 | 1.60 |

Figure 2:
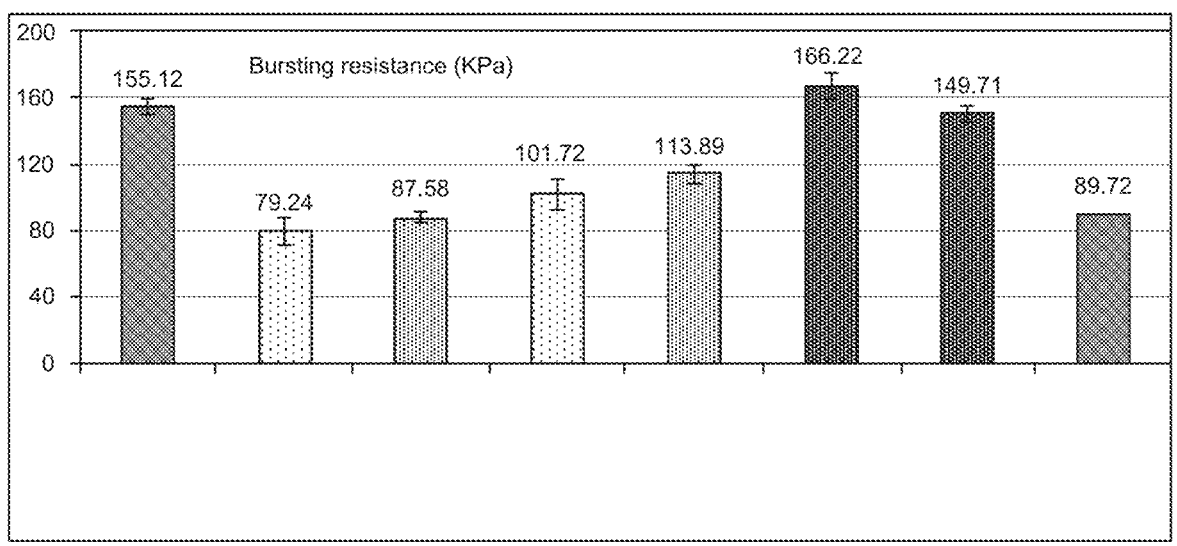
FIG. 2 is a graphical representation of the results obtained in the examples below.

Bursting resistance of the samples is also illustrated in FIG. 2. The bursting resistance is related to the stiffness of the product. Replacing softwood fibers with hardwood fibers, decreasing the amount of softwood fibers, decreasing the basis weight and adding cocoa extracts all can be used to decrease the stiffness of the product. Adding cocoa extracts increases the product stiffness by increasing its basis weight but it also improves its ability to be cut by making the product more flexible and dense.

Figure 3:
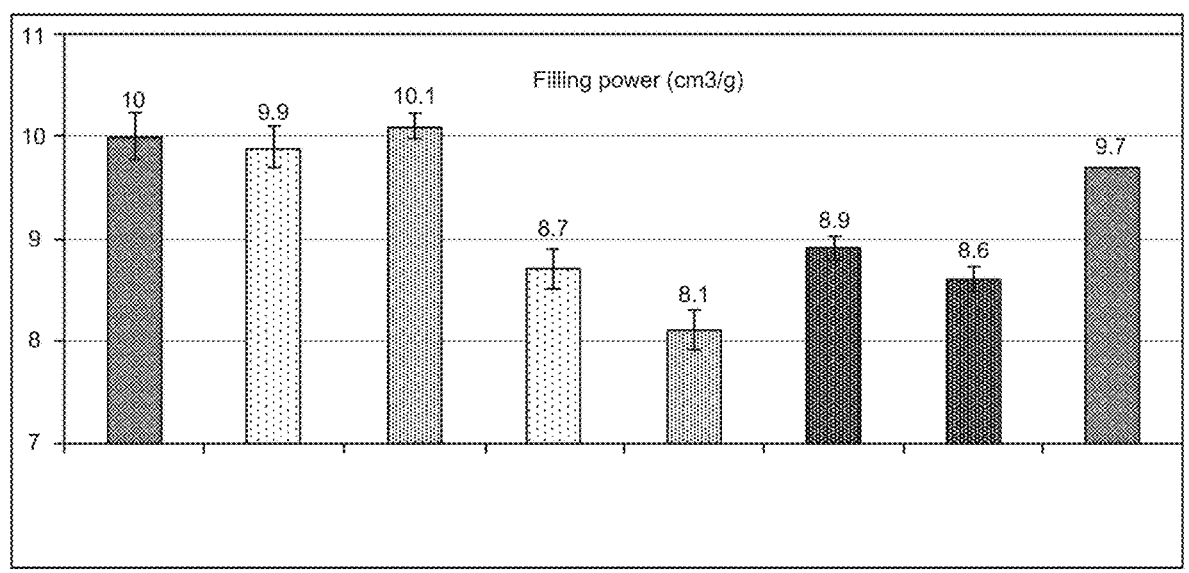
FIG. 3 is a graphical representation of the results obtained in the examples below.

The filling power of the reconstituted plant material samples is illustrated in FIG. 3.

Figure 4:
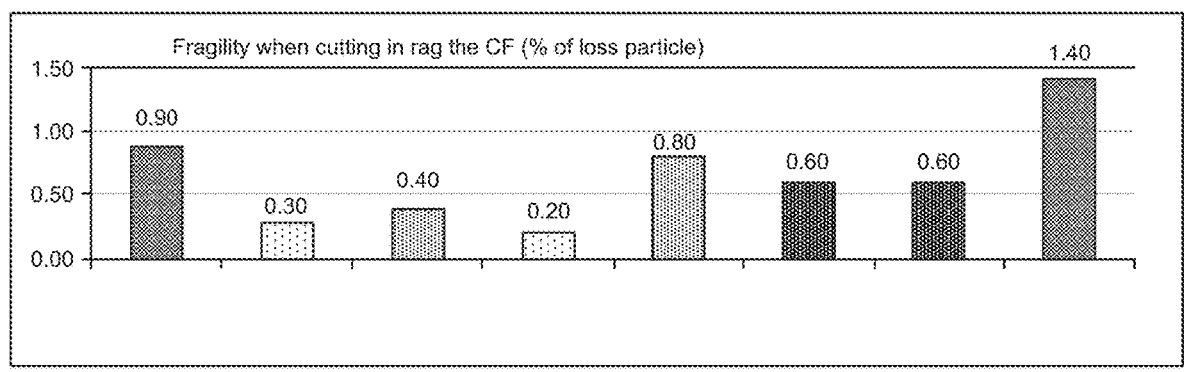
FIG. 4 is a graphical representation of the results obtained in the examples below.
Figure 5:
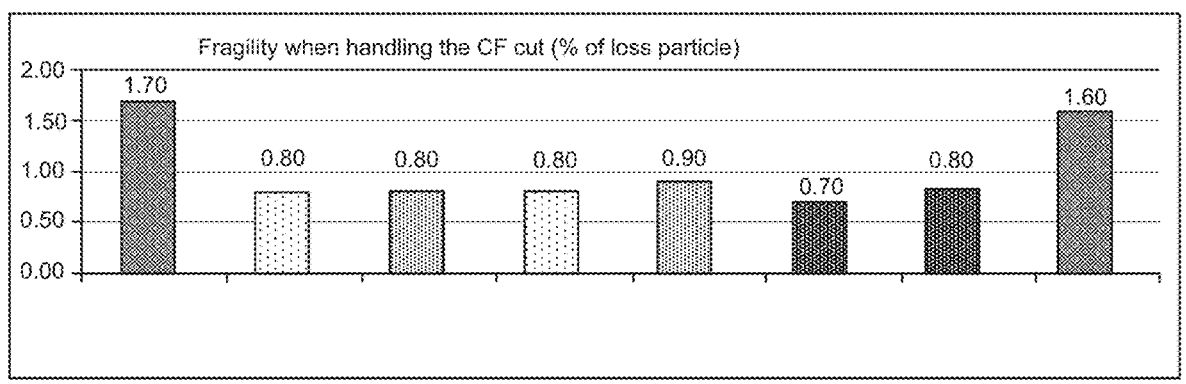
FIG. 5 is a graphical representation of the results obtained in the examples below.

Cutting fragility and handling fragility are shown in FIGS. 4 and 5. These tests demonstrate the particle loss when cutting the reconstituted plant material or handling the cut reconstituted plant material. As shown, Sample Nos. 2 through 7 all showed improvements in comparison to Sample No. 1 and Sample No. 8.

Based on the above results, the following reconstituted plant material samples were formulated and formed using commercial process equipment.

| | Sample No. 9 | Sample No. 10 | Sample No. 11 |
|---|---|---|---|
| Cocoa shells % | 67 | 56 | 47 |
| Total cellulose content % | 33 | 25 | 22 |
| Softwood content % | 33 | 15 | 13 |
| Hardwood content % | 0 | 10 | 9 |
| Refining level of pulp ° SR | 40 (minimum) | 75 | 75 |
| Cocoa extracts % (target) | 0 | 6 | 14 |
| Glycerin % | 0 | 7 | 5 |
| Calcium Carbonate filler % | 0 | 5 | 5 |
| Basic weight before the addition of the soluble gsm | 70 | 60 | 60 |
| Nicotine % | 0 | 0 | 0 |

In Sample No. 10 above, water soluble extracts were not applied to the reconstituted plant material. Water soluble extracts, however, were applied to the material in Sample No. 11 in a target amount of 21% by weight. As shown, Sample No. 10 contained residual water soluble extracts in an amount of 6% by weight, while Sample No. 11 contained extracts in an amount of 14% by weight. These amounts were measured after the reconstituted plant material was dry.

Figure 6:
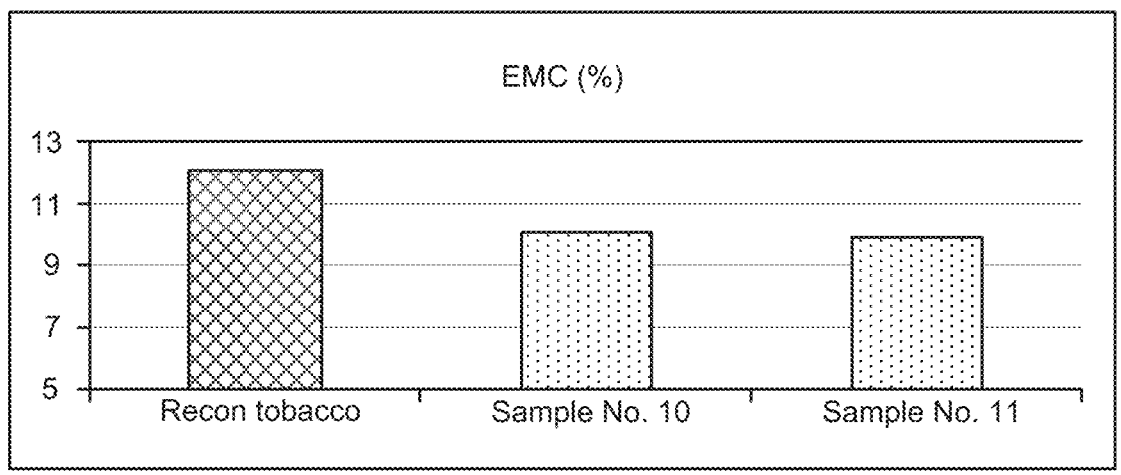
FIG. 6 is a graphical representation of the results obtained in the examples below.
Figure 7:
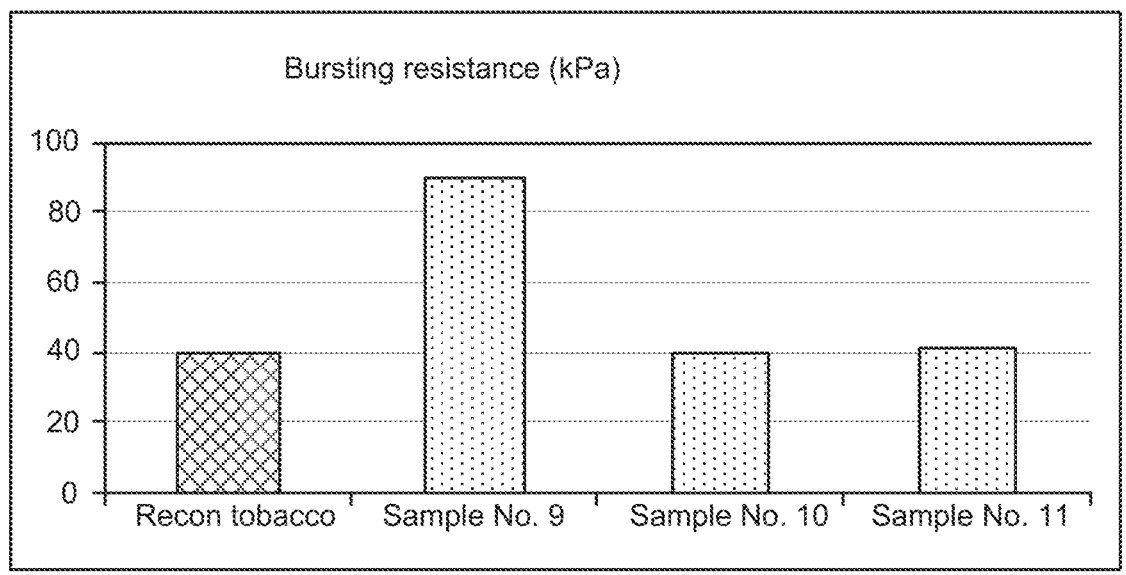
FIG. 7 is a graphical representation of the results obtained in the examples below.
Figure 8:
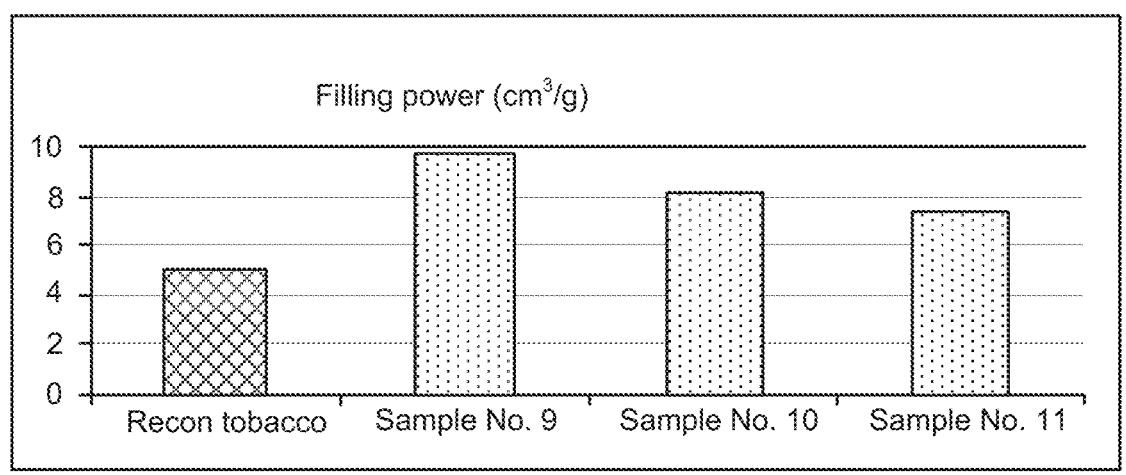
FIG. 8 is a graphical representation of the results obtained in the examples below.
Figure 9:
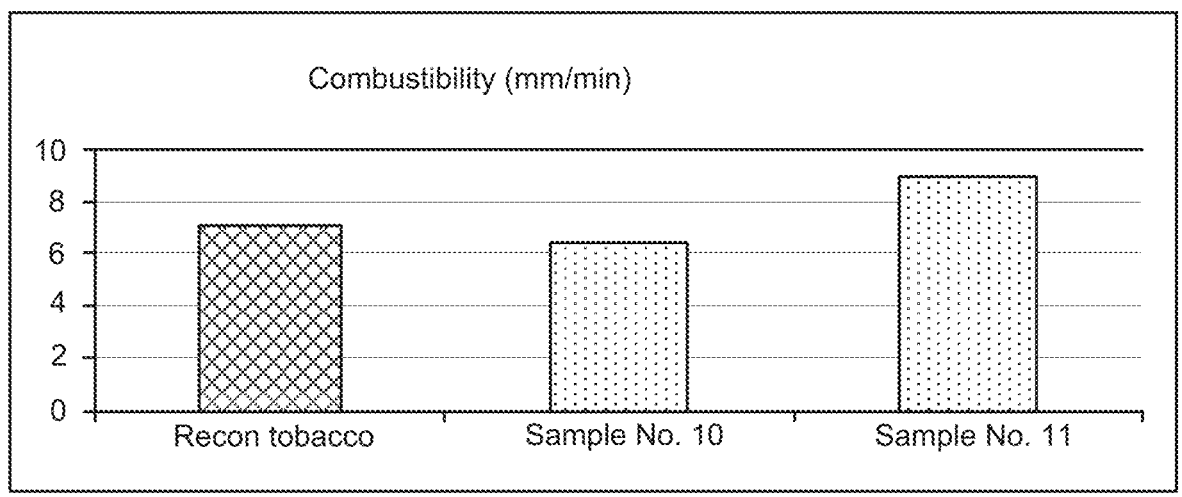
FIG. 9 is a graphical representation of the results obtained in the examples below.
Figure 10:
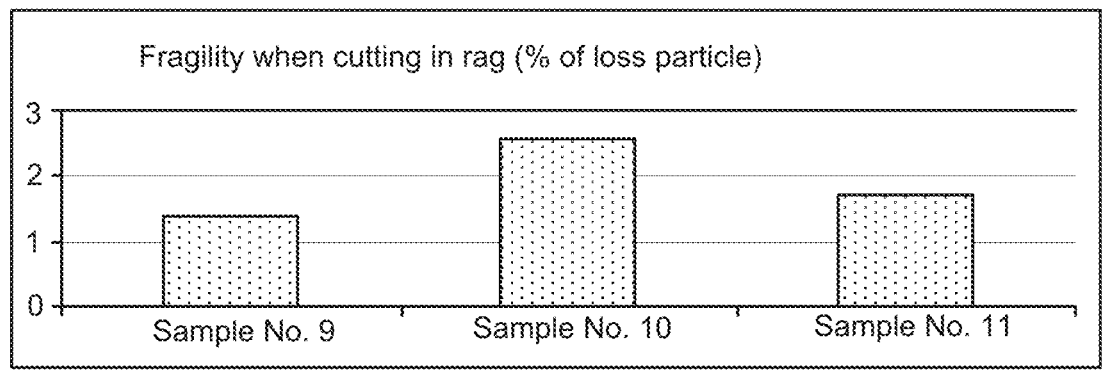
FIG. 10 is a graphical representation of the results obtained in the examples below.
Figure 11:
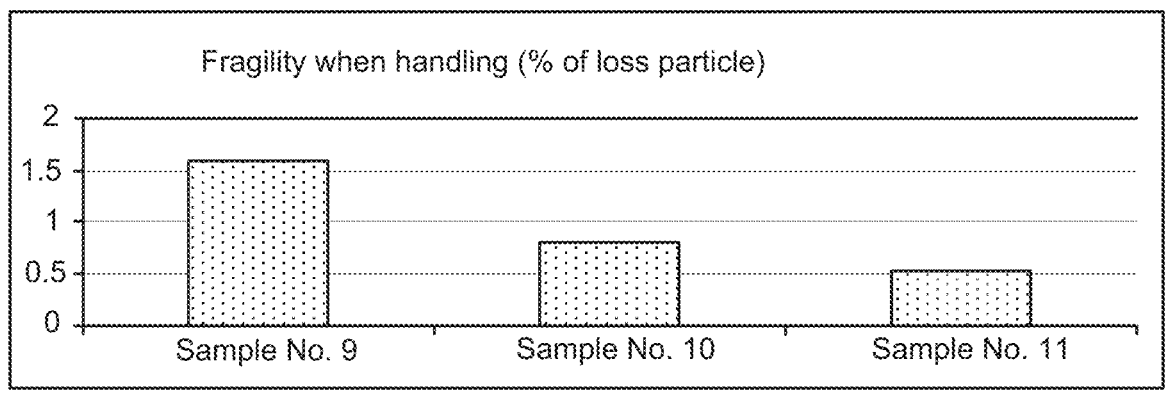
FIG. 11 is a graphical representation of the results obtained in the examples below.

Sample Nos. 9 through 11 were then tested for various properties and compared to a standard reconstituted material made from tobacco. For example, FIGS. 6 through 11 illustrate the results. FIG. 6 is directed to EMC percent which is the humidity of the product after being conditioned at least 48 hours at 22° C. and at a relative humidity of 60%. FIG. 7 illustrates bursting resistance, FIG. 8 illustrates filling power, FIG. 9 illustrates combustibility, FIG. 10 illustrates fragility when cutting and FIG. 11 illustrates fragility when handling.

As shown in the figures, the material of the present disclosure generally absorbs less moisture than a tobacco product. The figures also demonstrate that changing various parameters can reduce bursting resistance, decrease filling power and can have an impact on fragility.

Example 7

The following example demonstrates the ability to control mainstream smoke components when blending a cocoa filler made in accordance with the present disclosure with a standard tobacco filler.

A reconstituted cocoa filler was produced using generally the same method as described above with respect to Example 5. The reconstituted cocoa material contained 9% by weight softwood fibers, 9% by weight hardwood fibers, 5% by weight glycerine, 5% by weight calcium carbonate and the remainder cocoa material. Sixteen (16)% by weight cocoa extract was applied to the material.

The above reconstituted cocoa material was combined with a standard tobacco filler, American blend type. Five different samples were formulated in which the amount of the cocoa material in relation to the tobacco material was varied. The five samples are as follows:

Sample No. 1: 100% tobacco
Sample No. 2: 80% tobacco, 20% reconstituted cocoa material
Sample No. 3: 70% tobacco, 30% reconstituted cocoa material
Sample No. 4: 40% tobacco, 60% reconstituted cocoa material
Sample No. 5: 100% reconstituted cocoa material Each of the above samples was subjected to chemical analysis for determining the amount of various components contained within the material. In order to determine the amount of alkaloids in the material, Coresta Method No. 85 (April 2017) can be used. In order to determine the amount of nitrites and/or nitrates in the material, Coresta Method No. 36 (January 2015) can be used. In order to determine the amount of sugar in the material, Coresta Method No. 37 (August 2010) can be used.

The amount of tobacco specific nitrosamines can be determined using Coresta Method No. 72. In determining the TSNA amounts in the table below, Coresta Method No. 72 was modified as follows:

0.5 g of tobacco vs 1.0 g
50 ml of ammonium acetate containing internal standards instead of 30 ml
30 min of shaking vs 40 min (for free TSNA) The injection volume is 5 µl vs 10 µL
The flow rate is 0.35 ml/min vs 0.22 ml/min
D4-NAB not included, D4-NAT for NAT & NAB was used
Column: Waters X terra MS C18 2.1×50 mm dp 5 µm+pre-column Waters X terra C18 2.1×10 mm dp 3.5 µm
The following results were obtained.

|  |  | Sample No. 1 Standard tobacco | Sample No. 2 | Sample No. 3 | Sample No. 4 | Sample No. 5 conv w ext |
|---|---|---|---|---|---|---|
| Hot water solubles (precise) | % | 55.3 | 45.3 | 42 | 29.3 | 15.1 |
| Reducing sugar | % | 10.6 | 8.3 | 7.2 | 4.1 | 0.8 |
| Total alkaloids | % | 1.84 | 1.37 | 1.11 | 0.55 | isq |
| Nitrates | % | 0.67 | 0.49 | 0.42 | 0.28 | isq |
| Nitrites | ppm | isq | isq | isq | isq | isq |
| Potassium | % | — | — | — | — | 0.95 |
| TSNA Total | ppb | 2182 | 1639 | 999 | 455 | 0 |
| NNN N-nitrosonornicotine | ppb | 969 | 734 | 447 | 167 | 0 |
| NAT N'-nitrosoanatabine | ppb | 876 | 663 | 403 | 168 | 0 |
| NAB N-nitrosoanabasine | ppb | 51 | 45 | 28 | 22 | 0 |
| NNK Nitrosamine ketone | ppb | 286 | 197 | 121 | 98 | 0 |
| PG (Agilent) propylene glycol | % | 1.41 | 0.78 | 0.71 | 0.41 | 0.00 |
| Nicotine (Agilent) | % | 1.70 | 1.27 | 1.10 | 0.51 | 0.00 |
| Glycérine (Agilent) | % | 0.25 | 1.00 | 1.50 | 2.90 | 4.50 |
| Water (Agilent) | % | 12.70 | 9.70 | 9.20 | 8.30 | 7.20 |

Figure 12:
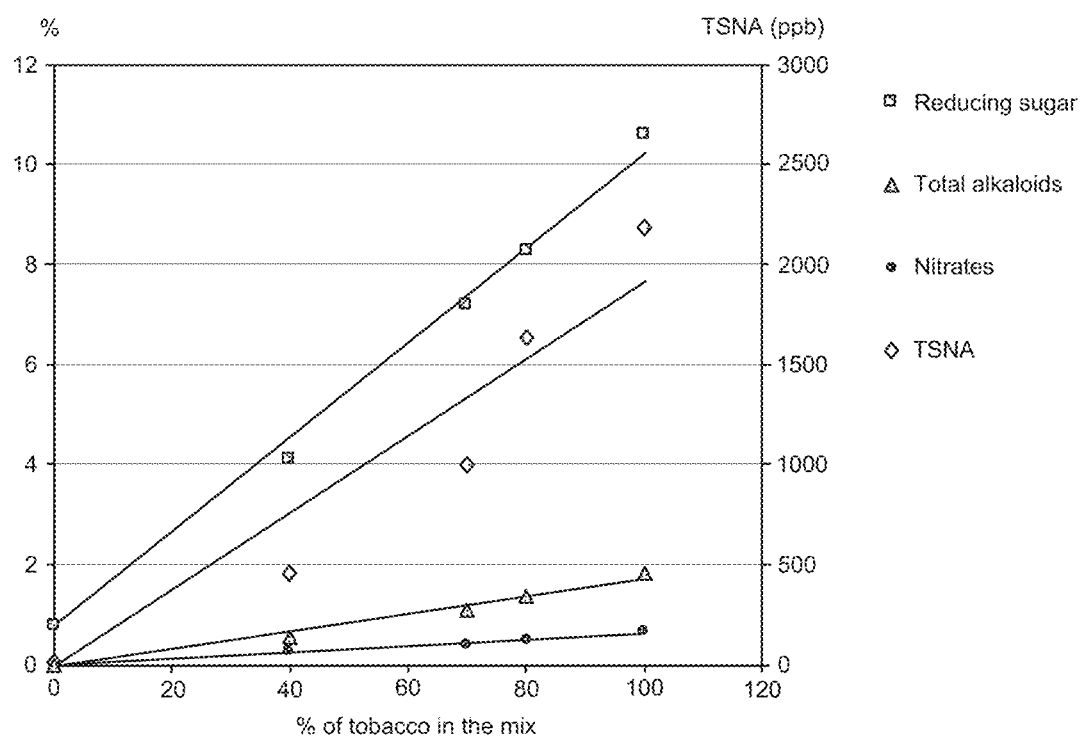
FIG. 12 is a graphical representation of the results obtained in the examples below.

FIG. 12 is a graphical representation of the amount of reducing sugar, total alkaloids, nitrates, and tobacco specific nitrosamines present in each blend as the percent of tobacco in the blend changes. As shown in FIG. 12, the various different components can be controlled by controlling the amount of tobacco in relation to the amount of the reconstituted cocoa material.

Figure 13:
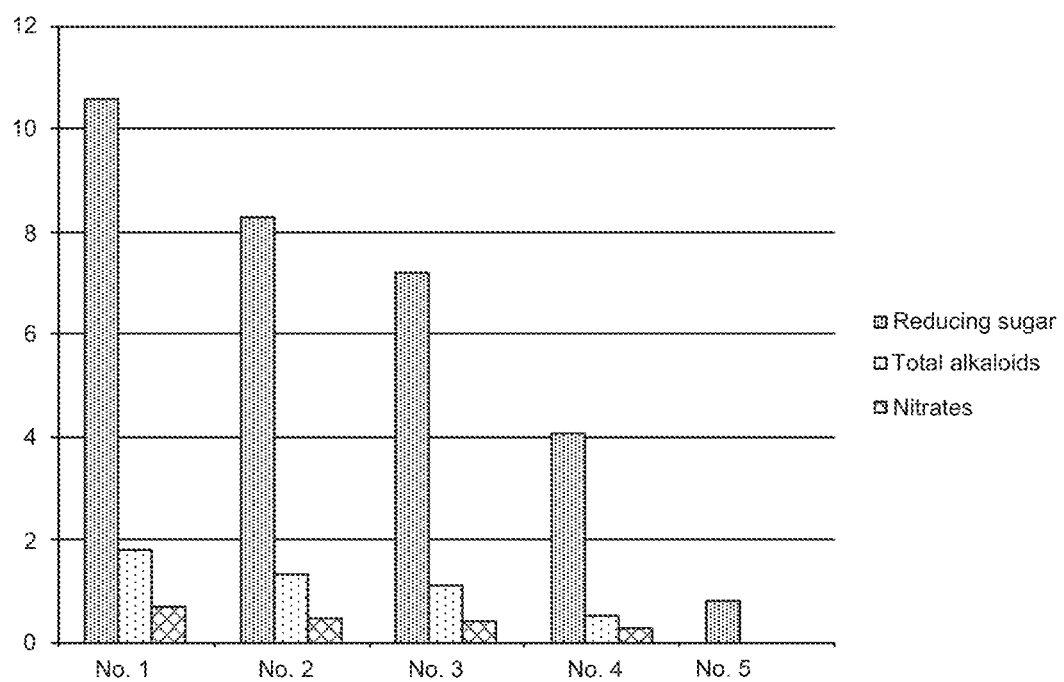
FIG. 13 is a graphical representation of the results obtained in the examples below.

FIG. 13 illustrates the amount of reducing sugar, total alkaloids and nitrates present in each sample.

Each of the samples were also made into cigarettes and an analysis of combustibility was performed. The following results were obtained.

|  |  | Sample No. 1 | Sample No. 2 | Sample No. 3 | Sample No. 4 | Sample No. 5 |
|---|---|---|---|---|---|---|
| Cigarette weight | mg | 969 | 1021 | 1016 | 1028 | 1036 |
| Standard pressure drop | mm WG | 90 | 97 | 100 | 102 | 104 |
| Static burn rate | mm/min | 6.80 | 5.60 | 5.80 | 6.40 | 6.60 |
| Puff number |  | 7.71 | 7.90 | 7.69 | 7.30 | 6.98 |
| TPM | mg/cig | 18.05 | 17.20 | 13.84 | 15.67 | 14.81 |
|  | mg/mg | 0.019 | 0.017 | 0.014 | 0.015 | 0.014 |
| Tar | mg/cig | 13.73 | 13.74 | 10.36 | 12.18 | 11.32 |
|  | mg/mg | 0.014 | 0.013 | 0.010 | 0.012 | 0.011 |
| Nicotine | mg/cig | 1.25 | 0.90 | 0.77 | 0.44 | bql |
|  | mg/mg | 0.0013 | 0.0009 | 0.0008 | 0.0004 | 0.0000 |
| Nicotine/tar | % | 9.08 | 6.58 | 7.40 | 3.60 | 0.14 |
| Water | mg/cig | 3.07 | 2.54 | 2.71 | 3.05 | 3.47 |
|  | mg/mg | 0.0032 | 0.0025 | 0.0027 | 0.0030 | 0.0033 |
| Tar/Puff | — | 1.78 |  | 1.35 | 1.67 | 1.62 |
| CO | mg/cig | 14.07 | 15.70 | 16.10 | 18.00 | 19.87 |
|  | mg/mg | 0.015 | 0.015 | 0.016 | 0.018 | 0.019 |
| CO/tar | — | 1.02 | 1.14 | 1.55 | 1.48 | 1.76 |
| CO/puff | — | 1.82 | 1.99 | 2.09 | 2.47 | 2.85 |

Figure 14:
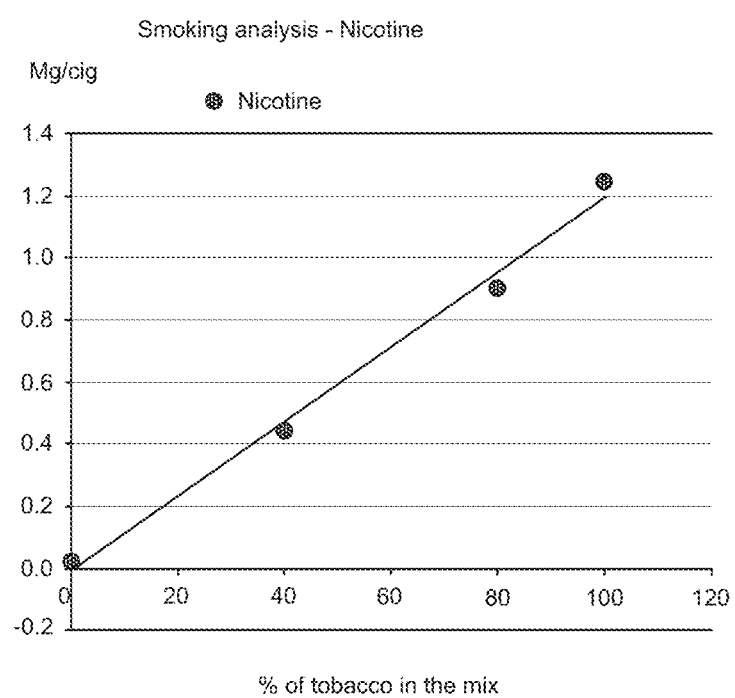
FIG. 14 is a graphical representation of the results obtained in the examples below.
Figure 15:
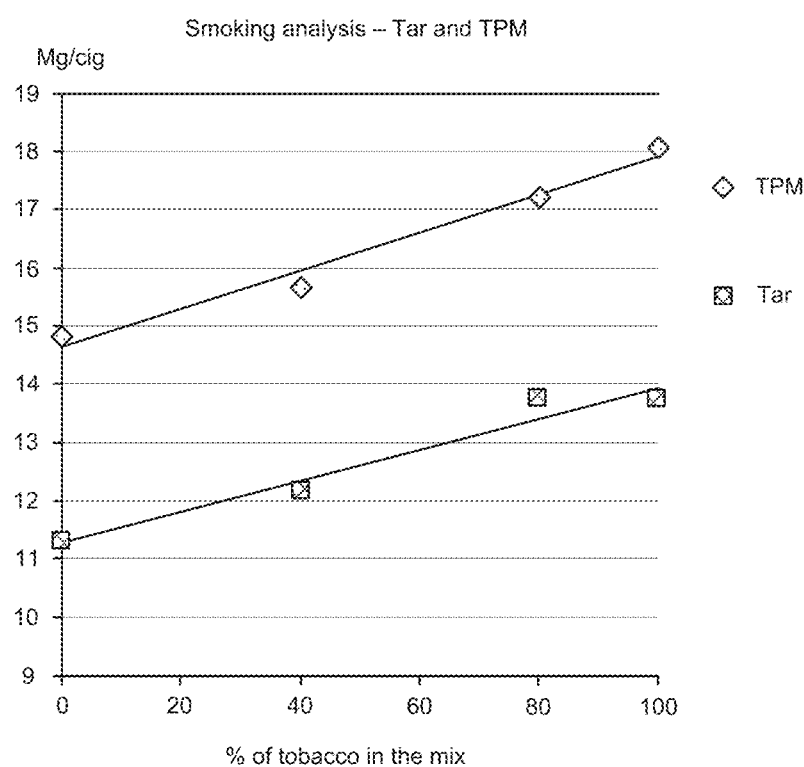
FIG. 15 is a graphical representation of the results obtained in the examples below.

FIGS. 14 and 15 are graphical representations of the results. FIG. 14 illustrates the reduction of nicotine as the amount of tobacco in the mix is reduced. Similarly, FIG. 15 shows that TPM and tar are reduced as the amount of tobacco in the mix is reduced. These results demonstrate how the reconstituted cocoa material can be used to control tar, nicotine, and TPM in smoking articles made from a blend of the reconstituted cocoa material and tobacco.

As described above, the aerosol generating material of the present disclosure can take many forms and be used in many products. In an embodiment, the aerosol generating material comprises a reconstituted cocoa husk material comprising extracted cocoa husk fibers combined with web building fibers. In an embodiment, the aerosol generating material further comprises an aerosol delivery composition containing an aerosol delivery agent. In an embodiment, the aerosol generating material may contain a humectant alone or in combination with the aerosol delivery composition. Any of the above embodiments can also contain water soluble cocoa husk components. The water soluble cocoa husk components can be obtained from the extracted cocoa husk fibers, optionally concentrated, and applied to the reconstituted material. The aerosol generating material can contain water soluble cocoa husk components, in an embodiment, in an amount of less than 15% by weight, such as less than about 10% by weight. In an alternative embodiment, the aerosol generating material can contain water soluble cocoa husk components in an amount greater than 10% by weight, such as in an amount greater than 15% by weight, such as in an amount from 10% by weight to 50% by weight.

In an embodiment, the aerosol generating material includes the reconstituted cocoa husk material containing extracted cocoa husk fibers and web building fibers treated with a humectant. The humectant can be glycerol, propylene glycol, or a combination of glycerol and propylene glycol. In an embodiment, the humectant may be present in the reconstituted cocoa husk material in an amount of about 8% by weight or less. In an alternative embodiment, the humectant may be present in the reconstituted cocoa husk material in an amount of about 8% by weight or greater, such as in an amount of about 10% by weight or greater, such as in an amount of about 15% by weight or greater, and generally in an amount of about 50% by weight or less.

In an embodiment, the aerosol generating material can include an aerosol delivery composition applied to the reconstituted plant material. The aerosol delivery composition contains an aerosol delivery agent. In an embodiment, the aerosol delivery agent comprises a drug or a flavorant. The aerosol delivery composition can be an oil, an aqueous solution, an aqueous dispersion, or a solid in any of the embodiments described herein. In an embodiment, the aerosol delivery agent comprises nicotine. In an embodiment, the aerosol delivery agent comprises a cannabinoid. In an embodiment, the aerosol delivery agent comprises tetrahydrocannabinol. In an embodiment, the aerosol delivery agent comprises cannabidiol. In an embodiment, the aerosol delivery agent comprises a combination of tetrahydrocannabinol and cannabidiol. Nicotine or a cannabinoid can also be combined with other aerosol delivery agents. In an embodiment, the other aerosol delivery agent is sugar. In an embodiment, the other aerosol delivery agent comprises a licorice extract. In an embodiment, the other aerosol delivery agent comprises honey. In an embodiment, the other aerosol delivery agent comprises coffee. In an embodiment, the other aerosol delivery agent comprises maple syrup. In an embodiment, the other aerosol delivery agent comprises a plant extract, such as a tea extract or a botanical extract. In an embodiment, the other aerosol generating agent comprises a tobacco extract. In an embodiment, the aerosol delivery agent comprises a tobacco extract alone. In an embodiment, the aerosol delivery composition contains a terpene or a blend of terpenes. A terpene or a blend of terpenes can be used with any of the aerosol delivery agents described above including nicotine or a cannabinoid.

The aerosol delivery composition containing one or more aerosol delivery agents can be present in the reconstituted cocoa husk material in an amount greater than about 1% by weight. In an embodiment, one or more aerosol delivery agents are present in an amount greater than about 3% by weight, such as in an amount greater than about 5% by weight. One or more aerosol delivery agents can be present on the reconstituted cocoa husk material in any of the embodiments described above in an amount less than about 50% by weight, such as in an amount less than about 25% by weight.

The web building fibers combined with the reconstituted plant material in any of the embodiments described above can vary. In an embodiment, the web building fibers are pulp fibers, such as softwood fibers, hardwood fibers, or mixtures thereof. In an embodiment, the web building fibers contain softwood fibers and hardwood fibers in a ratio of from 1:2 to 2:1. In an embodiment, the web building fibers comprise flax fibers. In an embodiment, the web building fibers are abaca fibers. In an embodiment, the web building fibers are bamboo fibers. In an embodiment, the web building fibers are coconut fibers. In an embodiment, the web building fibers are ramie fibers. In an embodiment, the web building fibers are jute fibers. In an embodiment, the web building fibers are hemp pulp fibers. The hemp pulp fibers can be used alone or in combination with wood pulp fibers, such as softwood fibers, hardwood fibers, or mixtures thereof. In an embodiment, the web building fibers are present in the aerosol generating material in an amount greater than about 3% by weight. In an embodiment, the web building fibers are present in the aerosol generating material in an amount greater than 5% by weight. In an embodiment, the web building fibers are present in the aerosol generating material in an amount greater than about 8% by weight. In an embodiment, the web building fibers are present in the aerosol generating material in an amount greater than about 12% by weight. In an embodiment, the web building fibers are present in the aerosol generating material in an amount greater than about 18% by weight. In an embodiment, the web building fibers are present in the aerosol generating material in an amount less than about 50% by weight, such as in an amount less than about 40% by weight.

In any of the above embodiments, the reconstituted cocoa husk material can further contain a filler. In an embodiment, the filler is calcium carbonate particles. In an embodiment, the calcium carbonate particles can be present in the reconstituted cocoa husk material in an amount from about 2% to about 10% by weight.

In an embodiment, the reconstituted cocoa husk material comprises extracted cocoa husk fibers, web building fibers, and a filler. The filler can be calcium carbonate particles. The web building fibers can be softwood fibers, hardwood fibers, or mixtures thereof. In an embodiment, the reconstituted cocoa husk material contains softwood fibers and hardwood fibers.

In an embodiment, the reconstituted cocoa husk material contains extracted cocoa husk fibers, web building fibers, a filler, a humectant, and water soluble cocoa husk components. In an embodiment, the reconstituted cocoa husk material contains 5% to 15% by weight softwood fibers, 5% to 15% by weight hardwood fibers, 3% to 8% glycerine, 3% to 10% calcium carbonate particles, and 10% to 30% by weight water soluble cocoa husk components. The remainder can comprise extracted cocoa husk fibers.

In any of the above embodiments, the extracted cocoa husk fibers and the web building fibers can be refined in an amount greater than 60° SR, such as greater than about 65° SR, such as greater than about 70° SR, such as greater than about 75° SR. The amount of refining can be less than about 95° SR.

In any of the above embodiments, the aerosol generating material can be in the form of a filler material comprised of a strip, strips, shreds, or mixtures thereof. The filler material can have a static burn rate of greater than 4 mm/mm, such as greater than 5 mm/mm. The filler material can have a filling power of greater than 4 cm$^3$/g, such as greater than 5 cm$^3$/g, such as greater than 6 cm$^3$/g.

In an embodiment, any of the embodiments of the aerosol generating material as described above, especially when in the form of a filler material, can be combined with a tobacco material. In an embodiment, the aerosol generating material is combined with a tobacco material comprising cut tobacco leaf. In an embodiment, the aerosol generating material is combined with a tobacco material comprising a reconstituted tobacco material. In still another embodiment, the aerosol generating material is combined with a cut leaf tobacco and a reconstituted tobacco material. In an embodiment, the aerosol generating material is combined with the tobacco material in order to control nicotine levels. The resulting blend can produce nicotine when smoked of less than 0.0008 mg/mg, such as less than 0.0006 mg/mg, such as less than 0.0004 mg/mg.

In any of the embodiments described above, the reconstituted cocoa husk material can be treated with a burn control agent, such as a salt of a carboxylic acid.

The aerosol generating material in any of the embodiments described above can be used in numerous different products. In an embodiment, the aerosol generating material of any of the above embodiments can be formed into a smokable rod surrounded by an outer wrapper to form a smoking article. The smoking article can optionally include a filter located at one end. Optionally, the wrapper can include a plurality of discrete reduced ignition areas.

In an embodiment, any of the aerosol generating materials described above can be used in a heat but not burn device.

In any of the aerosol generating material embodiments described above, the aerosol generating material can be used as a snuff product.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An aerosol generating material comprising:
   a reconstituted cocoa husk material comprising (1) extracted cocoa husk fibers combined with (2) web building fibers, the web building fibers comprising delignified cellulose fibers, the web budding fibers being present in the reconstituted cocoa husk material in an amount greater than about 15% by weight, and in an amount less than about 60% by weight, wherein the extracted cocoa husk fibers and the web building fibers are refined in an amount greater than about 60° SR and less than about 90° SR; and
   an aerosol delivery composition applied to the reconstituted cocoa husk material, the aerosol delivery composition containing an aerosol delivery agent and wherein the aerosol generating material comprises a filler material comprised of a strip, strips, shreds, or mixtures thereof of the reconstituted cocoa husk material.

2. An aerosol generating material as defined in claim 1, wherein the reconstituted cocoa husk material further comprises a humectant, wherein the humectant is present in the reconstituted cocoa husk material in an amount of about 10% by weight or greater and in an amount of about 50% or less.

3. An aerosol generating material as defined in claim 1, wherein the aerosol delivery agent comprises nicotine.

4. An aerosol generating material as defined in claim 1, wherein the aerosol delivery agent comprises a cannabinoid.

5. An aerosol generating material as defined in claim 1, wherein the aerosol delivery agent comprises tetrahydrocannabinol.

6. An aerosol generating material as defined in claim 1, wherein the aerosol delivery agent comprises cannabidiol.

7. An aerosol generating material as defined in claim 1, wherein the aerosol delivery composition contains a blend of terpenes.

8. An aerosol generating material as defined in claim 1, wherein the aerosol delivery composition is present on the reconstituted cocoa husk material in an amount greater than about 1% by weight and less than about 50% by weight.

9. An aerosol generating material as defined in claim 1, wherein the web building fibers are present in the reconstituted cocoa husk material in an amount greater than about 18% by weight, wherein the web building fibers comprise flax fibers, hemp fibers, abaca fibers, softwood fibers, hardwood fibers, bamboo fibers, coconut fibers, cotton fibers, kapok fibers, ramie fibers, jute fibers, or mixtures thereof.

10. An aerosol generating material as defined in claim 1, wherein the web building fibers comprise a combination of softwood fibers and hardwood fibers.

11. An aerosol generating material as defined in claim 1, wherein the reconstituted cocoa husk material contains filler particles, wherein the filler particles comprise calcium carbonate particles, the calcium carbonate particles present in an amount from about 2% to about 10% by weight.

12. An aerosol generating material as defined in claim 1, wherein the filler material has a static burn rate of greater than 4 mm/mm.

13. An aerosol generating material as defined in claim 1, wherein the filler material has a filling power of greater than 4 cm$^3$/g.

14. A smoking article comprising an outer wrapper surrounding a smokable rod, the smokable rod comprising the aerosol generating material of claim 1.

15. A smoking article as defined in claim 14, wherein the wrapper includes a plurality of discrete reduced ignition areas being spaced along an axial direction of the smoking article, the reduced ignition areas having a diffusivity of less than about 0.5 cm/s at 23° C.

16. A smoking article comprising a heating device and a chamber, the chamber containing the aerosol generating material as defined in claim 1, the heating device being positioned so as to heat the aerosol generating material for producing an inhalable aerosol without burning the aerosol generating material.

17. An aerosol generating material as defined in claim 1, wherein the reconstituted cocoa husk material comprises water soluble cocoa husk components in an amount from about 0.5% to about 50% by weight.

18. An aerosol generating material as defined in claim 1, wherein the reconstituted cocoa husk material has a basis weight from about 40 gsm to about 120 gsm.

19. An aerosol generating material comprising:
    a reconstituted cocoa husk material comprising (1) extracted cocoa husk fibers combined with (2) web building fibers, the web building fibers comprising delignified cellulose fibers, the web building fibers being present in the reconstituted cocoa husk material in an amount greater than about 15% by weight, and in an amount less than about 60% by weight, wherein the reconstituted cocoa husk material has a basis weight from about 40 gsm to about 120 gsm; and
    an aerosol delivery composition applied to the reconstituted cocoa husk material, the aerosol delivery composition containing an aerosol delivery agent and wherein the aerosol generating material comprises a filler material comprised of a strip, strips, shreds, or mixtures thereof of the reconstituted cocoa husk material.

20. An aerosol generating material comprising:
    a reconstituted cocoa husk material comprising (1) extracted cocoa husk fibers combined with (2) web building fibers, the web building fibers comprising delignified cellulose fibers, the web building fibers being present in the reconstituted cocoa husk material in an amount greater than about 15% by weight, and in an amount less than about 60% by weight; and an aerosol delivery composition applied to the reconstituted cocoa husk material, the aerosol delivery composition containing an aerosol delivery agent and wherein the aerosol generating material comprises a filler material comprised of a strip, strips, shreds, or mixtures thereof of the reconstituted cocoa husk material, wherein the filler material has a static burn rate of greater than 4 mm/mm.

21. An aerosol generating material comprising:

a reconstituted cocoa husk material comprising (1) extracted cocoa husk fibers combined with (2) web building fibers, the web building fibers comprising delignified cellulose fibers, the web building fibers being present in the reconstituted cocoa husk material in an amount greater than about 15% by weight, and in an amount less than about 60% by weight; and an aerosol delivery composition applied to the reconstituted cocoa husk material, the aerosol delivery composition containing an aerosol delivery agent and wherein the aerosol generating material comprises a filler material comprised of a strip, strips, shreds, or mixtures thereof of the reconstituted cocoa husk material, wherein the filler material has a filling power of greater than 4 $cm^3/g$.

\* \* \* \* \*